(12) United States Patent
Fujiwara

(10) Patent No.: US 10,107,808 B2
(45) Date of Patent: Oct. 23, 2018

(54) BIOSENSOR, CARTRIDGE STORING BIOSENSOR, MEASUREMENT DEVICE USING BIOSENSOR

(75) Inventor: Masaki Fujiwara, Ehime (JP)

(73) Assignee: PHC HOLDINGS CORPORATION, Tokyo (JP)

(*) Notice: Subject to any disclaimer, the term of this patent is extended or adjusted under 35 U.S.C. 154(b) by 1078 days.

(21) Appl. No.: 13/642,243

(22) PCT Filed: Jun. 20, 2011

(86) PCT No.: PCT/JP2011/003494
§ 371 (c)(1),
(2), (4) Date: Oct. 19, 2012

(87) PCT Pub. No.: WO2011/161926
PCT Pub. Date: Dec. 29, 2011

(65) Prior Publication Data
US 2013/0035573 A1    Feb. 7, 2013

(30) Foreign Application Priority Data

Jun. 23, 2010 (JP) .................................. 2010-142322

(51) Int. Cl.
*G01N 33/543* (2006.01)
*A61B 5/145* (2006.01)
(Continued)

(52) U.S. Cl.
CPC ....... *G01N 33/5438* (2013.01); *A61B 5/1468* (2013.01); *A61B 5/14532* (2013.01);
(Continued)

(58) Field of Classification Search
CPC ........... G01N 33/5438; G01N 27/3272; G01N 21/8483; A61B 5/14535; A61B 5/15113;
(Continued)

(56) References Cited

U.S. PATENT DOCUMENTS 8,221,336 B2    7/2012  Fujiwara et al.
2008/0047846 A1*  2/2008  Salzer ............... G01N 27/4168
205/778.5

(Continued)

FOREIGN PATENT DOCUMENTS

EP    1 854 410    11/2007
JP    9-168530    6/1997
(Continued)

OTHER PUBLICATIONS

International Search Report dated Sep. 13, 2011 in International (PCT) Application No. PCT/JP2011/003494.

(Continued)

*Primary Examiner* — Samuel P Siefke
(74) *Attorney, Agent, or Firm* — Wenderoth, Lind & Ponack, L.L.P.

(57) ABSTRACT

There are provided a biosensor, and a measurement device in which the biosensor is used, with which accurate puncture is enabled and reliability of measurement results are improved. The biosensor comprises an element substrate, a detector, a connection terminal, a continuity path, and a cutout. The detector is provided over the element substrate, and receives a specimen and detects a specific component contained in the specimen. The connection terminal is provided over the element substrate and acquires current corresponding to the specific component. The continuity path connects the connection terminal and the detector. The cutout is formed along the outer periphery of the detector so as to surround two or more directions of the detector.

18 Claims, 37 Drawing Sheets

(51) Int. Cl.
  *A61B 5/1468* (2006.01)
  *A61B 5/15* (2006.01)
  *A61B 5/151* (2006.01)
  *A61B 5/157* (2006.01)
  *C12Q 1/00* (2006.01)
  *G01N 27/327* (2006.01)
  *G01N 21/84* (2006.01)
  *A61B 5/1486* (2006.01)

(52) U.S. Cl.
  CPC ......... *A61B 5/14535* (2013.01); *A61B 5/157* (2013.01); *A61B 5/150022* (2013.01); *A61B 5/150061* (2013.01); *A61B 5/15113* (2013.01); *A61B 5/15186* (2013.01); *A61B 5/150358* (2013.01); *A61B 5/150412* (2013.01); *A61B 5/150519* (2013.01); *C12Q 1/001* (2013.01); *G01N 27/3272* (2013.01); *A61B 5/1486* (2013.01); *A61B 2562/0295* (2013.01); *G01N 21/8483* (2013.01)

(58) Field of Classification Search
  CPC ... A61B 5/1468; A61B 5/157; A61B 5/15186; A61B 5/14532; A61B 5/150519; A61B 5/150412; A61B 5/150358; A61B 5/150061; A61B 5/150022; A61B 5/1486; A61B 2562/0295; C12Q 1/001
  See application file for complete search history.

(56) References Cited

U.S. PATENT DOCUMENTS

| | | |
|---|---|---|
| 2008/0194988 A1 | 8/2008 | Nakamura et al. |
| 2009/0093735 A1 | 4/2009 | Korner et al. |
| 2009/0318790 A1 | 12/2009 | Fujiwara et al. |
| 2010/0324395 A1* | 12/2010 | Kitagawa ............. A61B 5/0059 600/345 |

FOREIGN PATENT DOCUMENTS

| | | |
|---|---|---|
| JP | 2006-314831 | 11/2006 |
| WO | 2008/035697 | 3/2008 |
| WO | 2009/098902 | 8/2009 |

OTHER PUBLICATIONS

Supplementary European Search Report dated Sep. 9, 2013 in corresponding European Application No. EP 11 79 7815.5.

* cited by examiner

BIOSENSOR, CARTRIDGE STORING BIOSENSOR, MEASUREMENT DEVICE USING BIOSENSOR

TECHNICAL FIELD

The present invention relates to a biosensor such as a blood glucose level sensor, and to a technique for utilizing a biosensor.

BACKGROUND ART

Biosensors for performing one-step puncture, blood collection, and measurement have been known in the past. A biosensor of this type has the following configuration, for example.

As shown in FIG. 29, a conventional biosensor 904 comprises an element substrate 909, a detector 910 provided over the element substrate 909, a connection terminal 911 provided to the outer peripheral end of the element substrate 909, and a continuity path 912 that connects the connection terminal 911 and the detector 910. Furthermore, the detector 910 has a puncture component 929, a specimen supply route 920 linked to the puncture component 929, and a reaction component 918 linked to the specimen supply route 920 (see Patent Literature 1, for example).

In use, the biosensor 904 is installed in a sensor installation component of a measurement device (not shown). Then, a finger 926 is placed under the puncture component 929 as shown in FIG. 30. At this point the portion of the measurement device surrounded by a negative pressure formation component 906 is placed under negative pressure. A needle 907 is then moved toward the puncture component 929.

In the state shown in FIG. 30, part of the finger 926 bulges up when the contact portion between the biosensor 904 and the finger 926 is put under negative pressure by the negative pressure formation component 906. The needle 907 punctures this bulging portion. Blood that flows out of this puncture is deposited in a blood guide 930 of the biosensor 904 by the force of the negative pressure. The blood then reaches a reaction component 918 through the specimen supply route 920. The reaction component 918 is coated with a reagent. The blood reacts with this reagent in the reaction component 918, a current corresponding to the blood glucose level is produced, and the measurement device measures the blood glucose level on the basis of this current.

CITATION LIST

Patent Literature

Patent Literature 1: WO2008-035697

SUMMARY

With the above-mentioned conventional biosensor, measurement reliability issues were encountered for the following reasons.

In the above-mentioned prior art, the bulging portion of the finger was pressed strongly against the biosensor 904 by the negative pressure formation component 906. As a result, even after the finger 906 was punctured by the needle 907, the blood did not always flow out in sufficient quantity. For example, since the height of the skin that bulges up under negative pressure varies from one individual to the next, a person with soft skin (whose skin more readily bulges up) will have higher contact pressure with the sensor, and in this state the blood tends not to flow when the skin is punctured. That is, with a conventional biosensor, there was a great individual difference related to the bulging of the skin under a specific negative pressure, and the positional relation and contact pressure between the punctured site of the finger and the sensor could not be kept constant. As a result, measurement could not be carried out properly, and the measurement result was not reliable.

In view of this, it is an object of the present invention to the skin to be punctured properly and to improve reliability of the measurement result.

To achieve the stated object, the biosensor of the present invention comprises an element substrate, a detector provided over the element substrate and configured to receive a specimen and detect a specific component contained in the specimen, a connection terminal provided over the element substrate and configured to acquire current corresponding to the specific component, a continuity path arranged to connect the connection terminal and the detector, and a cutout formed along an outer periphery of the detector so as to surround two or more directions of the detector.

Because the above-mentioned biosensor comprises a cutout formed along the outer periphery of the detector so as to surround two or more directions of the detector, contact pressure with respect to the finger produced by negative pressure in the detector can be suitably released so that the skin can be punctured properly, which improves the reliability of the measurement result.

With the biosensor of the present invention, the skin can be punctured properly and the reliability of the measurement result can be improved.

DETAILED DESCRIPTION

1. Embodiment 1

1.1 Measurement Device

Figure 1:
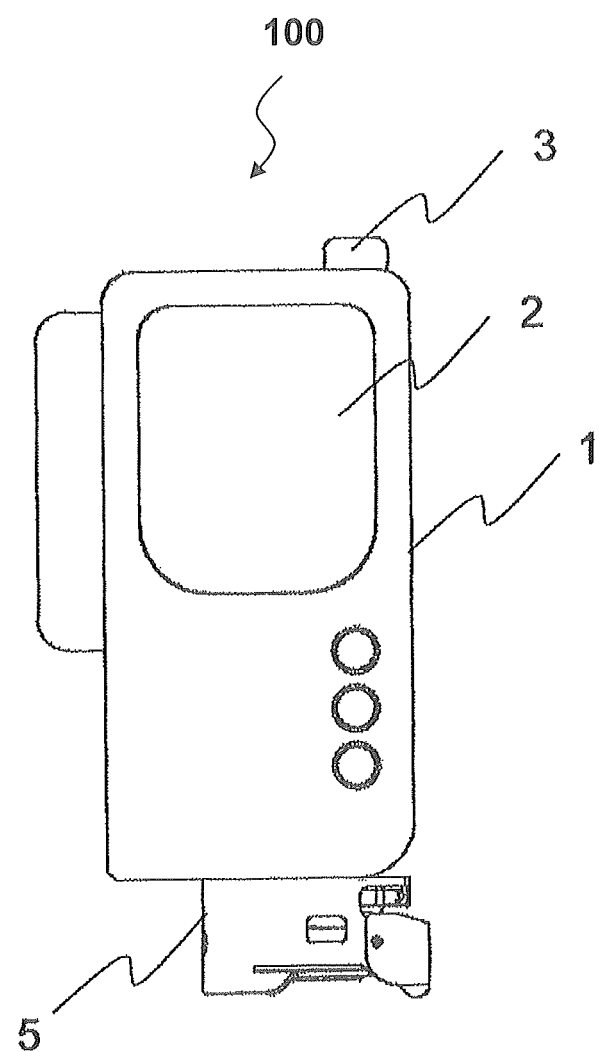
FIG. 1 is a front view of the measurement device pertaining to an embodiment of the present invention.

FIG. 1 shows a measurement device 100 pertaining to Embodiment 1 of the present invention. The measurement device 100 is comprised of a main case 1 that is taller than it is wide and is configured to be held in a user's hand, a display component 2 provided to the front face of the main case 1, a puncture button 3 provided to the top part of the main case 1, a sensor installation component 5 of a biosensor 4 provided to the bottom part of the main case 1, a negative pressure formation component 6 for putting the sensor installation component 5 under negative pressure (FIGS. 6 to 9), and a needle movement component 8 for moving a needle 7 with respect to the negative pressure formation component 6 (FIGS. 6 to 9).

The measurement device 100 in this embodiment is used as follows. The user holds the main case 1 in one hand (such as the right hand), and presses a finger (such as the index finger of the left hand) under the sensor installation component 5. When the user presses the puncture button 3 in this state, a puncture operation is carried out as shown in FIGS. 6 to 9 (discussed below).

1.2 Biosensor

1.2.1 Configuration of Biosensor

Figure 2:
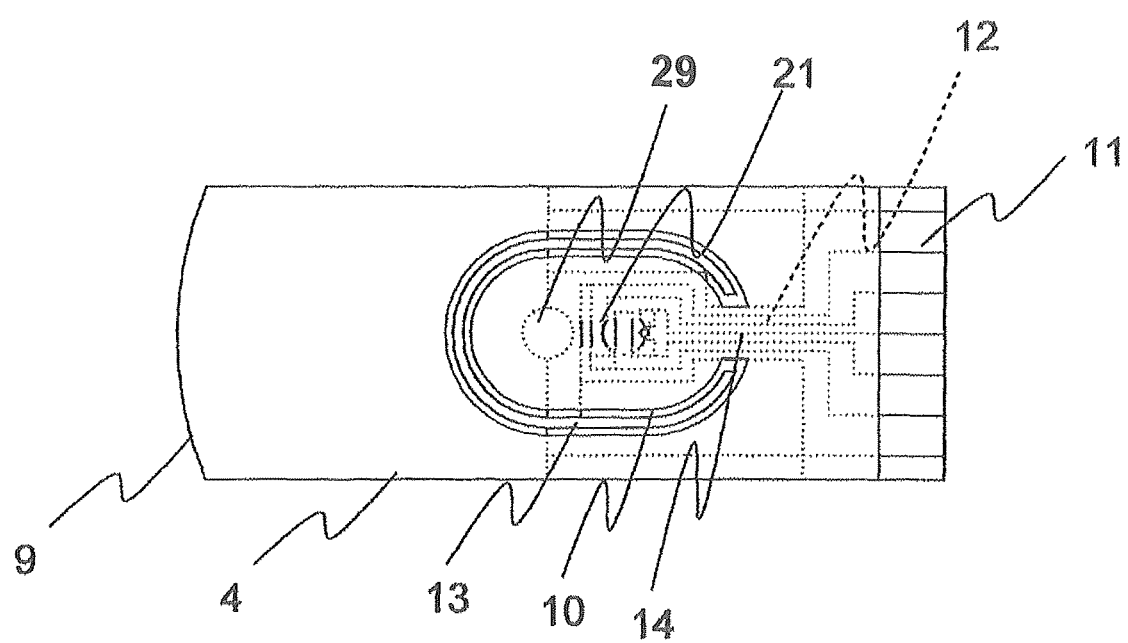
FIG. 2 is a plan view of the biosensor pertaining to Embodiment 1 of the present invention.

FIG. 2 shows the configuration of the biosensor 4 pertaining in this embodiment. Ten of these biosensors 4, for example, are stacked and held in the sensor installation component 5 of the measurement device 100 shown in FIG. 1. The biosensors 4 are installed so that they can be automatically fed out one at a time to the position shown in FIGS. 6 to 9.

As shown in FIG. 2, the biosensor 4 comprises a rectangular element substrate 9, a substantially elliptical detector 10 provided over the element substrate 9, a connection terminal 11 provided at an end in the long-side direction of the element substrate 9, and a continuity path 12 that connects the connection terminal 11 and the detector 10.

The element substrate 9 further has a substantially elliptical cutout 13 formed along the outer periphery of the detector 10 so as to surround the detector except for the pull-out portion of the continuity path 12.

The continuity path 12 connects the elliptical detector 10 and the connection terminal 11. The continuity path 12 connects the detector 10 and the connection terminal 11 through a non-cutout part 14 in which the cutout 13 is not formed. The width of the non-cutout part 14 is narrower than the width in the short-side direction of the elliptical detector 10.

The connection terminal 11, for example, has two or more detecting electrodes disposed for detecting a component of blood (the specimen). The detecting electrodes include a pair of electrodes consisting of a working electrode and a counter electrode. The "working electrode" here is an electrode for measuring a blood component (an example of biological information), and the "counter electrode" is an electrode that is paired with the working electrode. Furthermore, the detecting electrodes preferably include a "detecting electrode" that is used to detect whether or not blood has been supplied to a reaction component 18 (discussed below). The detecting electrodes may also include an "Hct electrode" for measuring the hematocrit value in blood.

The connection terminal 11 is electrically connected to a controller (not shown) provided inside the main case 1 of the measurement device 100.

Figure 3:
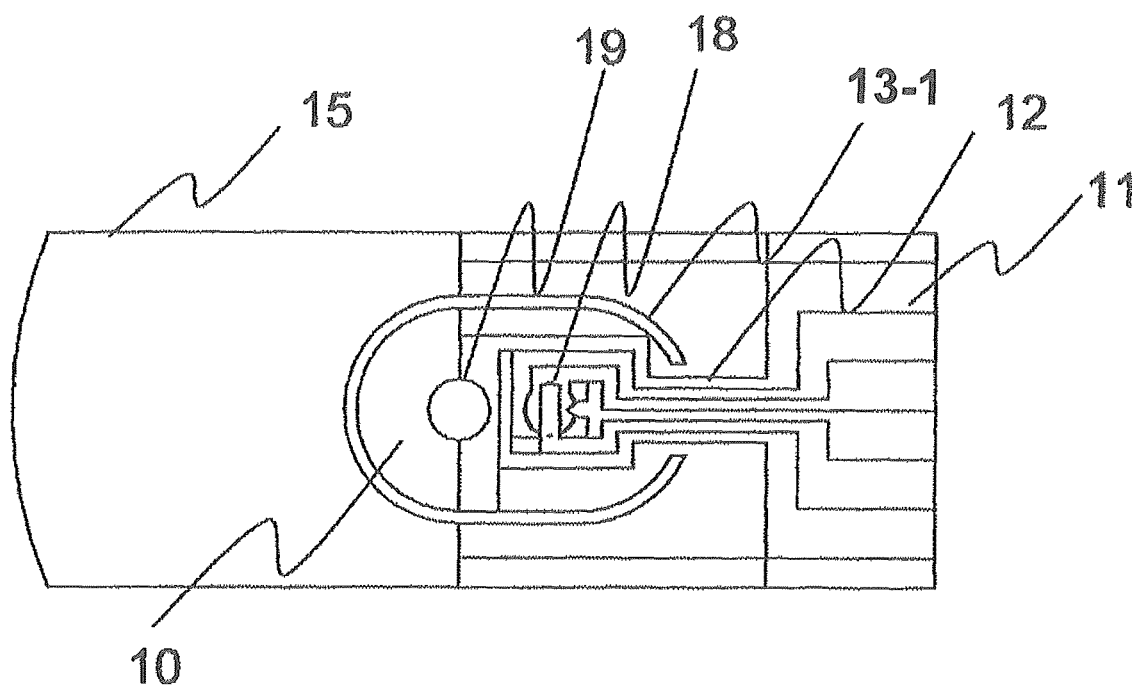
FIG. 3 is a plan view of part of the biosensor.
Figure 4:
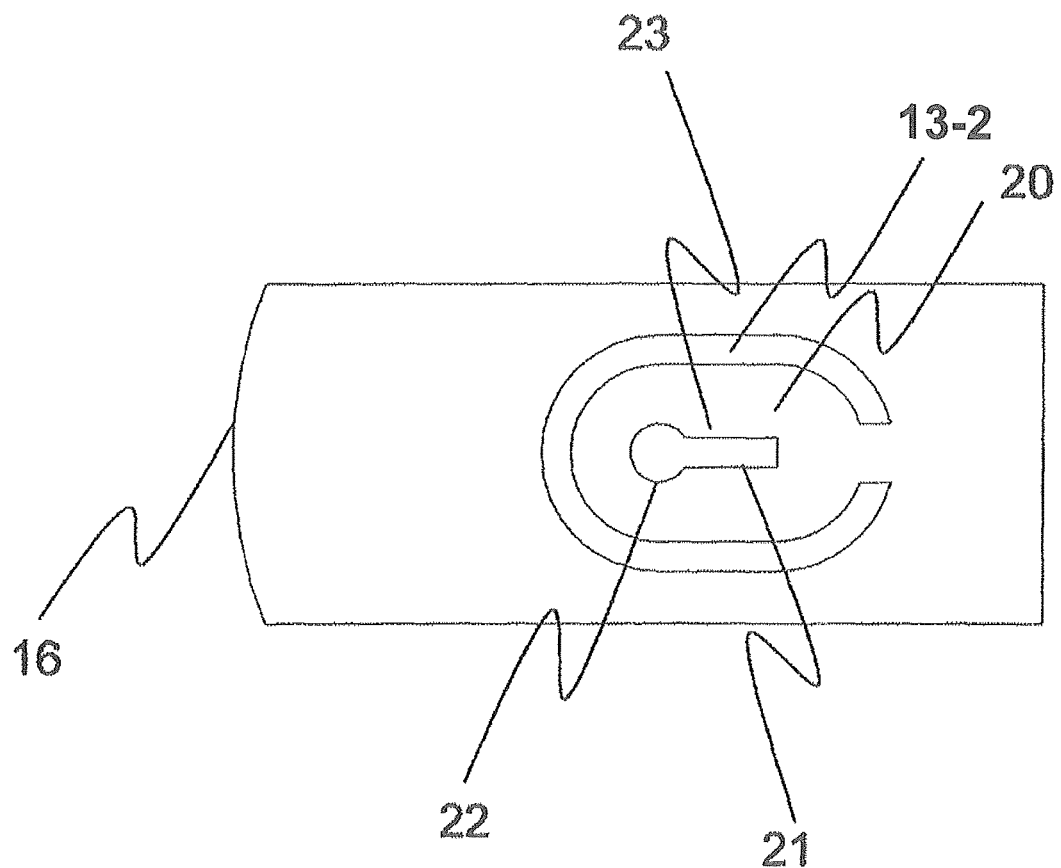
FIG. 4 is a plan view of part of the biosensor.
Figure 5:
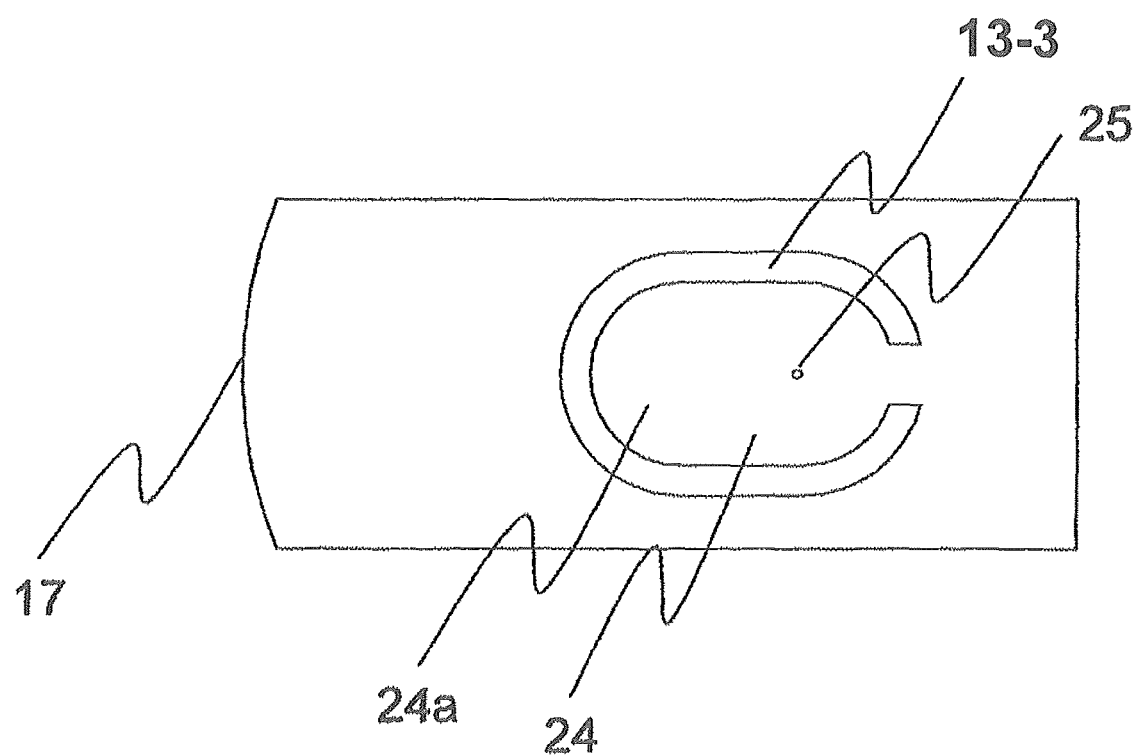
FIG. 5 is a plan view of part of the biosensor.

The biosensor 4 is constituted by laminating the three plates shown in FIGS. 3 to 5, respectively. That is, the element substrate 9 of the biosensor 4 is constituted by laminating a rectangular lower plate 15 (FIG. 3), a rectangular middle plate 16 provided over the lower plate 15 (FIG. 4), and a rectangular upper plate 17 provided over the middle plate 16 (FIG. 5), in that order from bottom to top.

The lower plate 15 includes a cutout 13-1 having substantially the same shape as the cutout 13, an elliptical reaction component 18 provided on the inside of the cutout 13-1, the continuity path 12, and the connection terminal 11. The detector 10 provided with the reaction component 18 is elliptical in shape as mentioned above. A circular puncture through-component 19 (an example of a through-component) constituting part of a puncture component 29 (FIG. 2) is provided on the opposite side of the pull-out portion of the continuity path 12 from the center position of the elliptical detector 10.

The reaction component 18 is coated with a reagent for detecting the blood glucose level, for example. When blood is deposited on this reagent, a response current is produced by a redox reaction, which is a signal from the biosensor 4 in the reaction component 18. This response current is transmitted through the continuity path 12 and the connection terminal 11 to the measurement device 100. With the measurement device 100, the response current is converted into voltage, this voltage value is converted into a specific digital value by A/D conversion, and is then inputted to the controller. The controller measures blood concentration data, such as the hematocrit concentration or the glucose concentration (indicating the blood glucose level), on the basis of the digital value. After this, the blood glucose level is displayed as a measurement value on the display component 2. This blood glucose level measurement, display on the display component 2, and so forth are all known topics discussed in detail in the above-mentioned Patent Literature 1 and elsewhere, and therefore will not be described in detail herein.

Next, the middle plate 16 shown in FIG. 4 is provided with a cutout 13-2 that has substantially the same shape as the cutout 13 and is wider than the cutout 13-1. Accordingly, the outer periphery of an elliptical spacer 20 provided on the inside of the cutout 13-2 is smaller than the outer periphery of the detector 10 of the lower plate 15. A specimen supply route 21 is formed in the spacer 20. As shown in FIG. 4, the specimen supply route 21 is comprised of a puncture through-hole 22 (an example of a through-component) at a position corresponding to the puncture through-component 19 of the lower plate 15, and a narrow groove 23 that communicates with the puncture through-hole 22 and the reaction component 18 of the lower plate 15. The puncture through-hole 22 constitutes part of the puncture component 29 (FIG. 2).

The upper plate 17 shown in FIG. 5 is provided with a cutout 13-3 that has substantially the same shape as the cutout 13 and is wider than the cutout 13-1. Accordingly, the outer periphery of an elliptical cover 24 provided on the inside of the cutout 13-3 is smaller than the outer periphery of the detector 10 of the lower plate 15. The cover 24 has an air hole 25 formed so as to communicate with the portion of the narrow groove 23 of the spacer 20 in the middle plate 16 that is on the opposite side from the puncture through-hole 22. A non-through-component 24a (an example of a non-through-component) is formed in the portion of the cover 24 of the upper plate 17 at a position corresponding to the puncture through-component 19 of the lower plate 15 and the puncture through-hole 22 of the middle plate 16. The non-through-component 24a constitutes part of the puncture component 29 (FIG. 2), and the needle 7 shown in FIGS. 6 to 9 punctures this non-through-component 24-1.

The lower plate 15, middle plate 16, and upper plate 17 shown in FIGS. 3 to 5, respectively, are laminated in that order from bottom to top to form the biosensor 4 shown in FIG. 2. Of the cutout 13-1, cutout 13-2, and cutout 13-3 formed in the lower plate 15, middle plate 16, and upper plate 17, respectively, the cutout 13-2 and the cutout 13-3 are formed wider than the cutout 13-1. When the lower plate 15, the middle plate 16, and the upper plate 17 are laminated, the outer periphery of the detector 10 of the lower plate 15 is the widest, slightly to the inside of which the spacer 20 is positioned, and the cover 24 is also laminated thereon. Providing a difference in the sizes of the cutouts 13 between the plates is also related to the non-cutout part 14 shown in FIG. 2. That is, as shown in FIG. 3, since the continuity path 12 is provided at the non-cutout part 14 of the lower plate 15, this portion must be sufficiently wide (the width in a direction perpendicular to the pull-out direction of the continuity path 12) for the continuity path 12 to be arranged. On the other hand, the width of the non-cutout part 14 of the middle plate 16 covering the continuity path 12, and of the non-cutout part 14 in the upper plate 17 (the width in a direction perpendicular to the pull-out direction of the continuity path 12), is narrower than the width of the non-cutout part 14 of the lower plate 15. This will be described later, but is an effective configuration in that the detector 10 readily bends upward. The length of the middle plate 16 and the upper plate 17 is shorter than that of the lower plate 15, resulting in a state in which the connection terminal 11 is exposed at the right end of the lower plate 15 as shown in FIG. 2.

1.2.2 Operation of Biosensor

Figure 6:
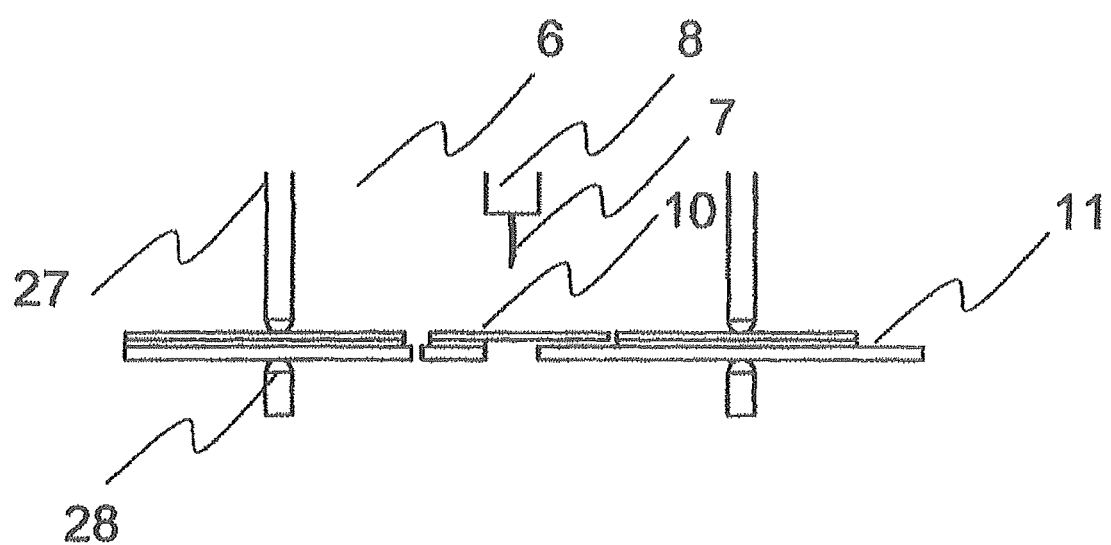
FIG. 6 is a cross section of the main components in a state in which the biosensor pertaining to Embodiment 1 has been placed in a measurement device.
Figure 8:
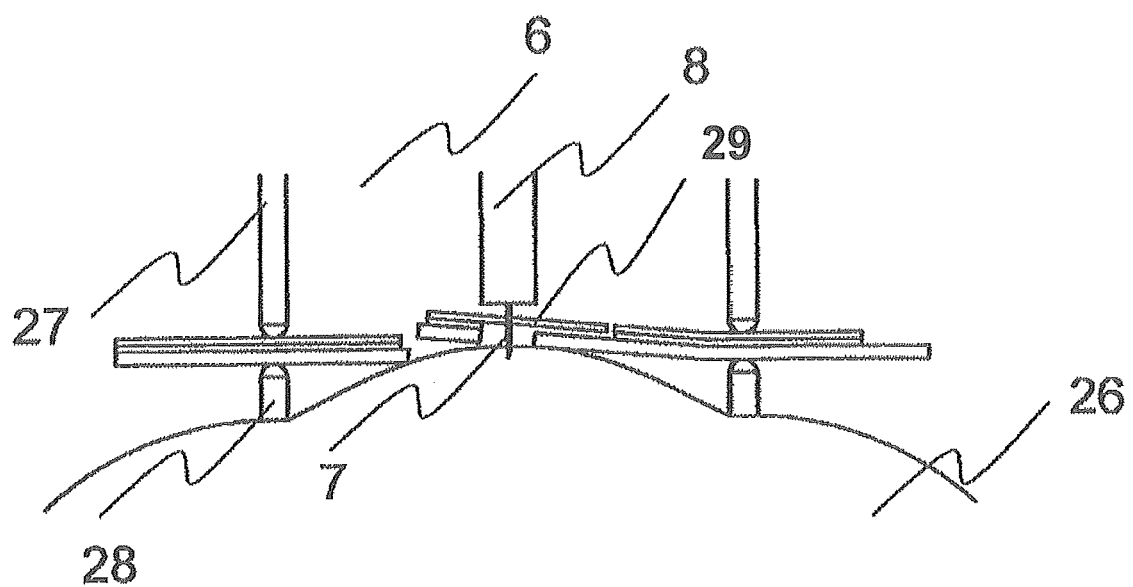
FIG. 8 is a cross section of these main components.
Figure 9:
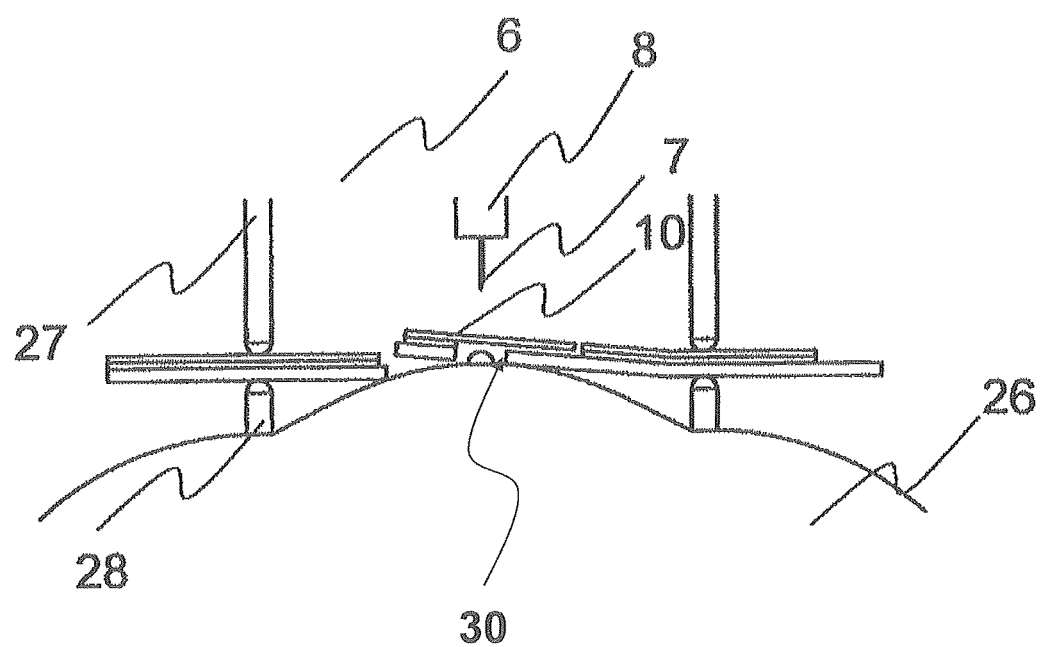
FIG. 9 is a cross section of these main components.
Figure 10:
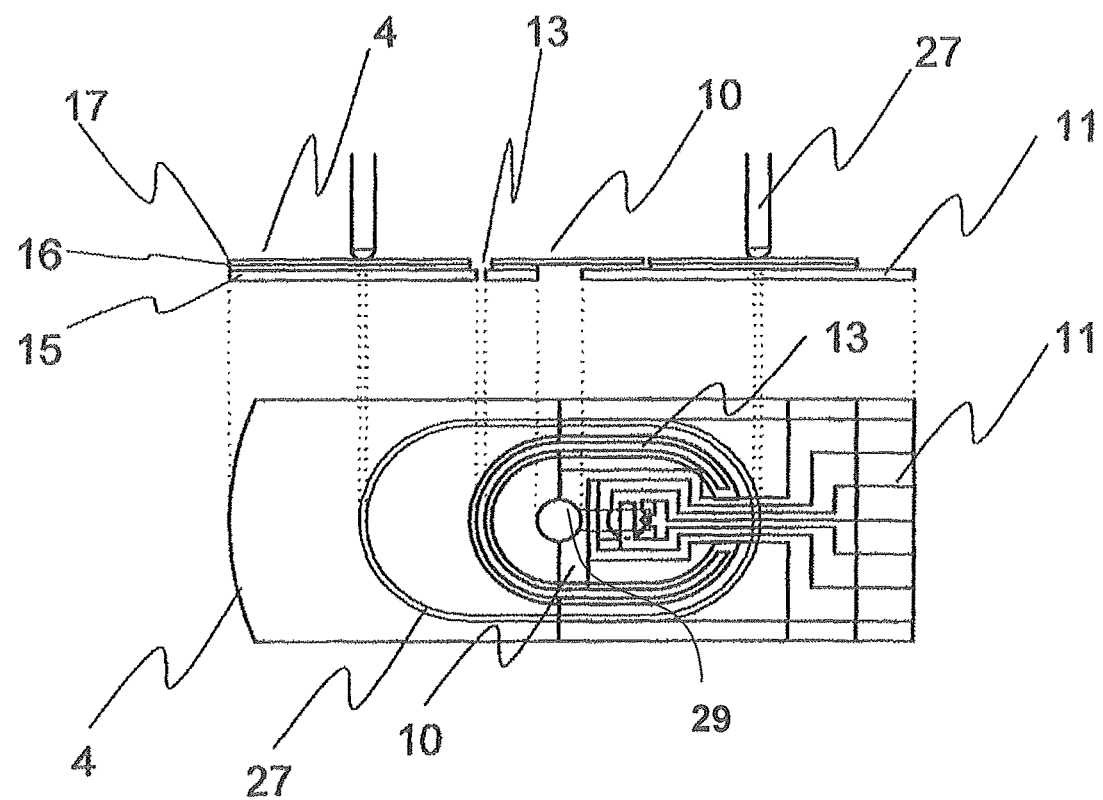
FIG. 10 is a diagram of the relative relation of the components when the above-mentioned biosensor has been installed in the measurement device.

When the blood glucose level is measured with the measurement device 100 shown in FIG. 1, first the biosensors 4 are installed at the sensor installation component 5 of the measurement device 100. At this point, as shown in FIG. 10, the upper face of the biosensor 4 is pressed by an upper cylinder 27, which is the negative pressure formation component 6 and surrounds the detector 10 outside the cutout 13. The lower face of the biosensor 4 is also pressed by a lower cylinder 28, which is the negative pressure formation component 6 and surrounds the detector 10 outside the cutout 13, as shown in FIG. 6. The operation shown in FIGS. 6 to 9 is carried out in this state.

As shown in FIG. 10, the puncture component 29 here is preferably located in the center of the space (negative pressure chamber) in which negative pressure is formed by the negative pressure formation component 6. The result of this is that the top of the skin of the finger that bulges up under negative pressure is positioned at the puncture component 29, which affords more reliable puncture.

Next, the finger 26 of the user is pressed under the biosensor 4 installed in the sensor installation component 5 of the measurement device 100. Negative pressure is generated by the negative pressure formation component 6 in this state, causing part of the finger 26 to bulge up.

Figure 7:
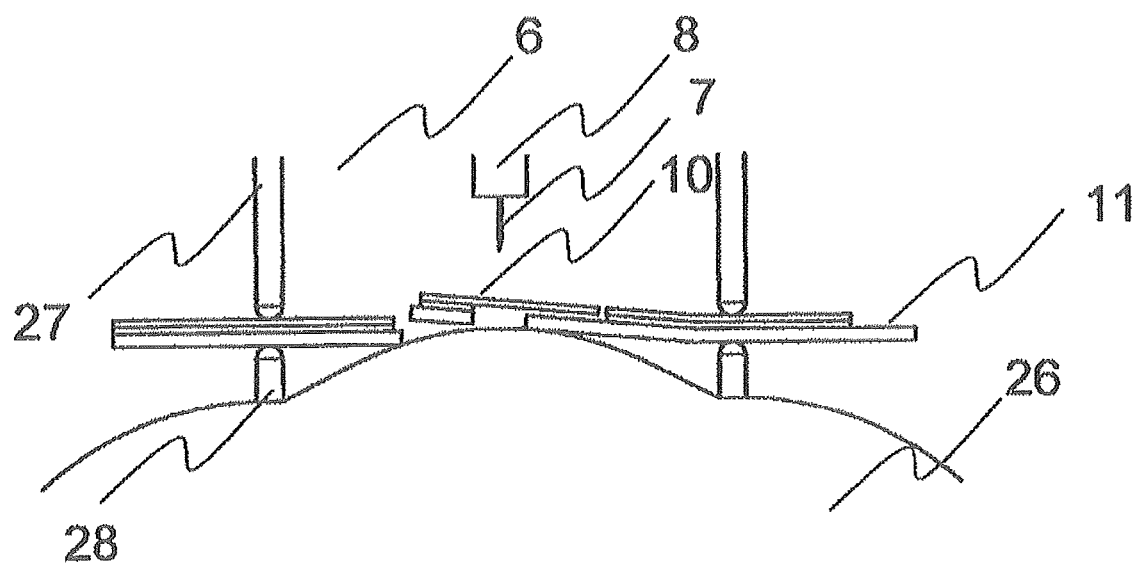
FIG. 7 is a cross section of these main components.

If the skin bulges up very much due to the skin being soft or some other reason, and the contact pressure between the biosensor 4 and the finger 26 reaches a specific level or higher, the inside of the cutouts 13 of the biosensor 4 (that is, the detector 10) bends upward as shown in FIG. 7, relieving the excess contact pressure. As shown in FIG. 8, when the needle 7 is moved downward by the needle movement component 8 in this state, the needle 7 passes through the puncture through-component 19 and punctures the finger 26. Then, as shown in FIG. 9, when the needle 7 is moved upward by the needle movement component 8, blood flows out of the finger 26. This blood is deposited on a blood guide 30 of the biosensor 4 by the force of negative pressure. The blood is then supplied through the specimen supply route 21 to the reaction component 18, current corresponding to blood glucose level produced in the reaction component 18 is transmitted through the continuity path 12 and the connection terminal 11 to a controller (not shown) provided inside the main case 1 shown in FIG. 1, where the blood glucose level is calculated. After this, the blood glucose level is displayed as a measurement value on the display component 2.

1.3 Features of Biosensor

The features of the embodiment described above will now be described.

Figure 11:
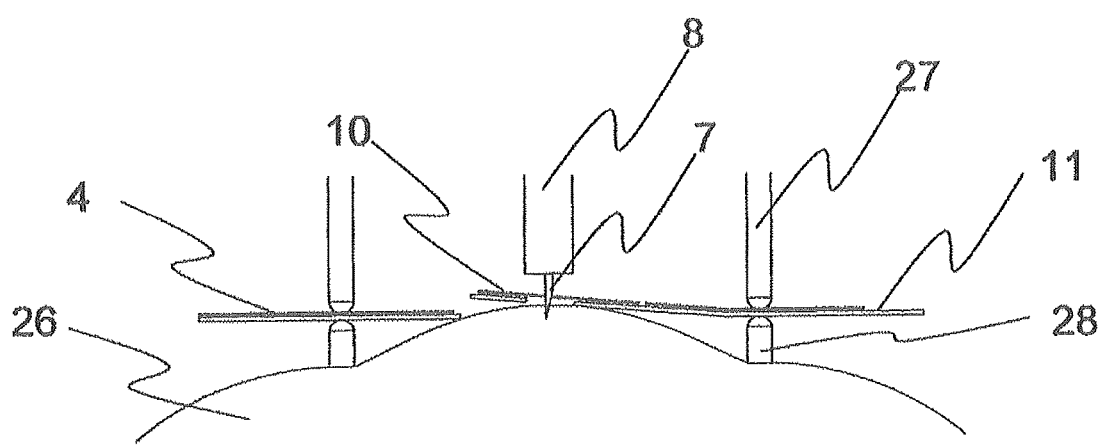
FIG. 11 is a cross section of the main components of the biosensor and the measurement device during the puncture operation.
Figure 12:
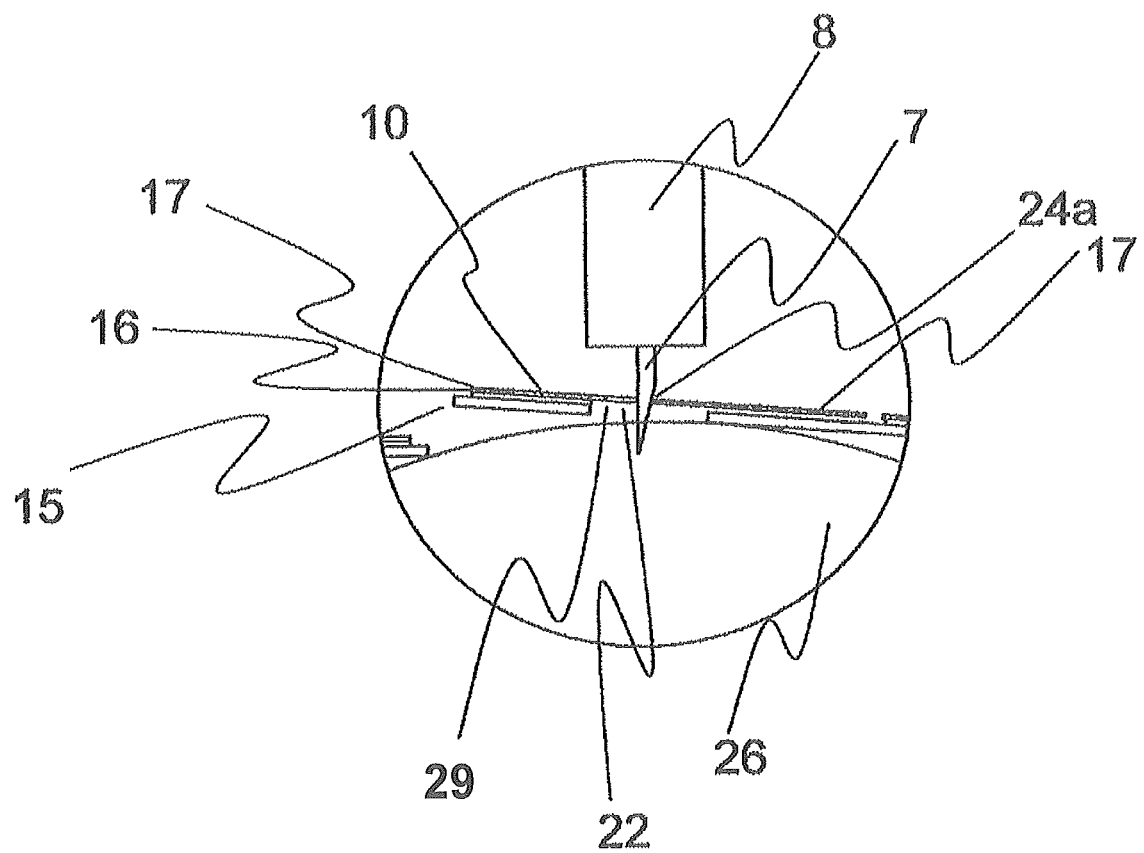
FIG. 12 is an enlarged view of the main components in FIG. 11.

As shown in FIG. 11, in a state in which part of the finger 26 has bulged upward under negative pressure, the detector 10 is lifted upward (that is, moved away) on the opposite side from the connection terminal 11 in the inside portion of the cutout 13 of the biosensor 4. That is, even if part of the finger 26 bulges upward under negative pressure, this bulging portion (that is, the puncture site) is not pressed against the biosensor 4. In this state, as shown in FIG. 12, the needle 7 is moved downward by the needle movement component 8, and the finger 26 is punctured by the needle 7 via the puncture component 29 (the non-through-component 24-1 of the upper plate 17, the puncture through-hole 22 of the middle plate 16, and the puncture through-component 19 of the lower plate 15). After this, when the needle 7 is moved upward by the needle movement component 8, blood flows from the finger 26. As a result, the detection of the blood glucose level is carried out properly.

In other words, in this embodiment, the detector 10 and the blood guide 30 of the biosensor 4 that are held within the negative pressure component are formed so that they can move away from the element substrate 9, which allows the contact pressure between the biosensor 4 and the skin to be kept constant, and enough blood for measurement to flow out upon proper puncture. As a result, the reliability of the measurement result can be improved.

As to the non-cutout part 14 of the biosensor 4, as shown in FIG. 3, since the continuity path 12 is provided to the portion of the lower plate 15 corresponding to the non-cutout part 14, this portion is also wide enough to provide the continuity path 12 (the width in a direction perpendicular to the pull-out direction of the continuity path 12). On the other hand, the portion of the middle plate 16 (which covers the continuity path 12) corresponding to the non-cutout part 14, and the portion of the upper plate 17 corresponding to the non-cutout part 14 have a width (the width in a direction perpendicular to the pull-out direction of the continuity path 12) that is narrower than the width of the portion of the lower plate 15 corresponding to the non-cutout part 14. Accordingly, the non-cutout part 14 is formed so that the width above is narrower than from below. As a result, the detector 10 readily and smoothly bends upward. Therefore, contact pressure of the finger on the biosensor 4 is suitably released, the skin can be punctured properly, and the reliability of the measurement result can be improved.

1.4 Modification Examples

Modification examples of Embodiment 1 will now be described. Portions having the same configuration and function as in the above embodiment will be numbered the same and will not be described again.

1.4.1 Modification Example 1

Figure 13:
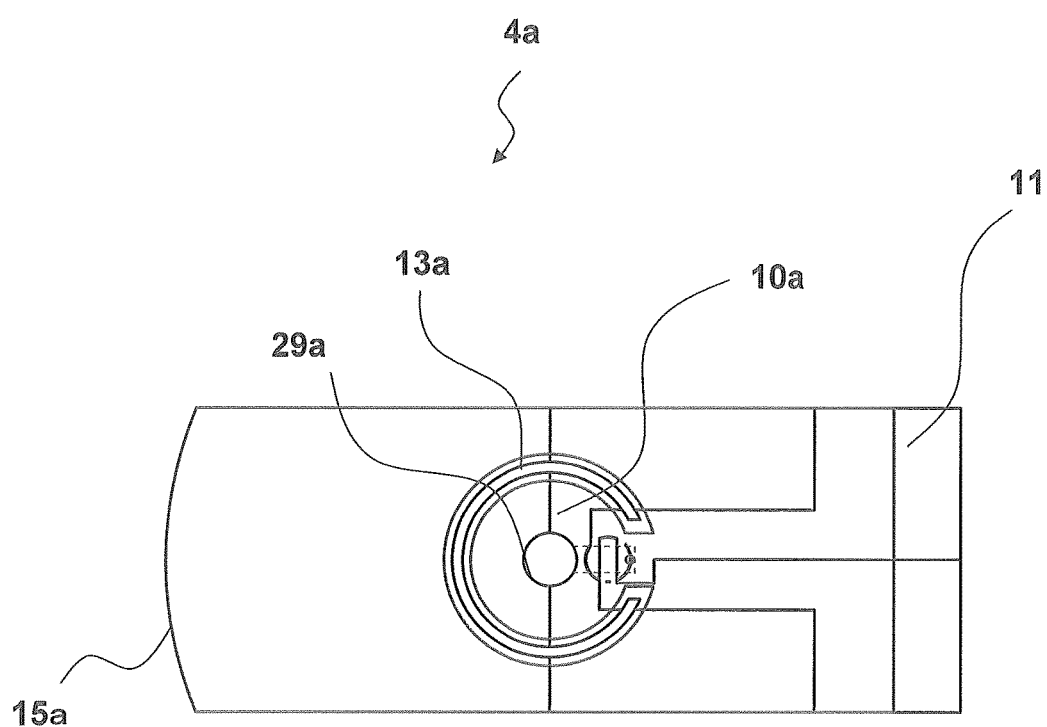
FIG. 13 is a plan view of the biosensor pertaining to a modification example of Embodiment 1.

FIG. 13 shows a biosensor 4a in Modification Example 1. Modification Example 1 differs from Embodiment 1 above in that a detector 10a of a lower plate 15a shown in FIG. 13 is circular, and the cutout 13a around the outer periphery thereof is also substantially circular. When the circular detector 10a is thus provided, a puncture component 29a is provided in the approximate center of the circular detector 10a. The cutouts in the middle plate and upper plate that are laminated in that order over the lower plate 15a are also substantially circular.

Because the biosensor 4a has the above configuration, the negative pressure part formed by the negative pressure formation component 6, that is, the airtight area, can be smaller, and the puncture operation can be carried out more effectively.

1.4.2 Modification Example 2

Figure 14:
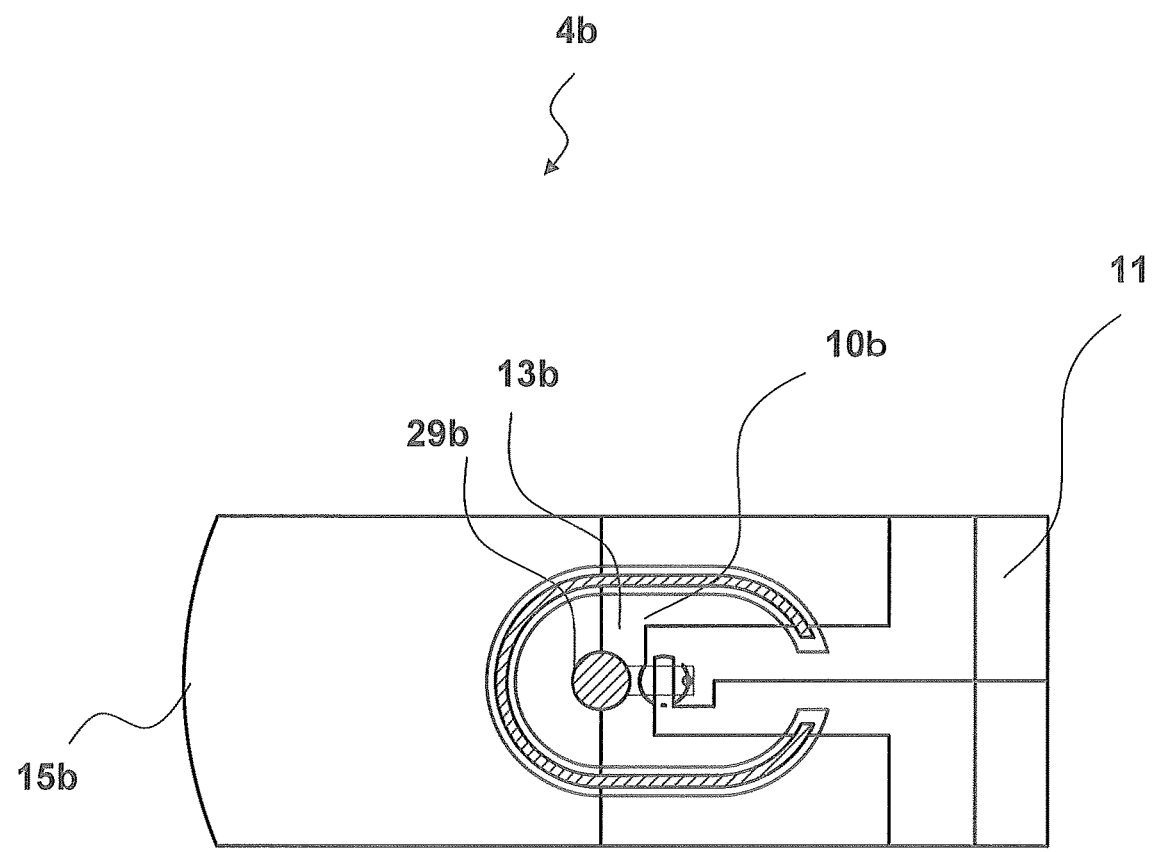
FIG. 14 is a plan view of the biosensor pertaining to another modification example of Embodiment 1.

FIG. 14 shows a biosensor 4b in Modification Example 2. In Modification Example 2, as shown in FIG. 14, the distance is longer between the portion of a lower plate 15b where a detector 10b bends, and the puncture component 29. The middle plate and upper plate that are laminated in that order over this also have a shape that corresponds to the lower plate 15b.

Because the biosensor 4b has the above configuration, the angle at which the detector 10b bends is gentler, so the detector 10b will be able to bend even when the finger contact pressure is low.

1.4.3 Modification Example 3

In Embodiment 1 above, the lower plate 15, the middle plate 16, and the upper plate 17 were provided, and the specimen supply route 21 is formed in the middle plate 16, but this is not the only option. Alternatively, a lower plate and an upper plate are provided, a reaction component, a continuity path, and a connection terminal are provided over the lower plate, and a specimen supply route is formed between the lower plate and the upper plate. Also, a puncture through-hole is formed over the lower plate, and a non-through-component is formed on the upper plate.

2. Embodiment 2

Figure 15:
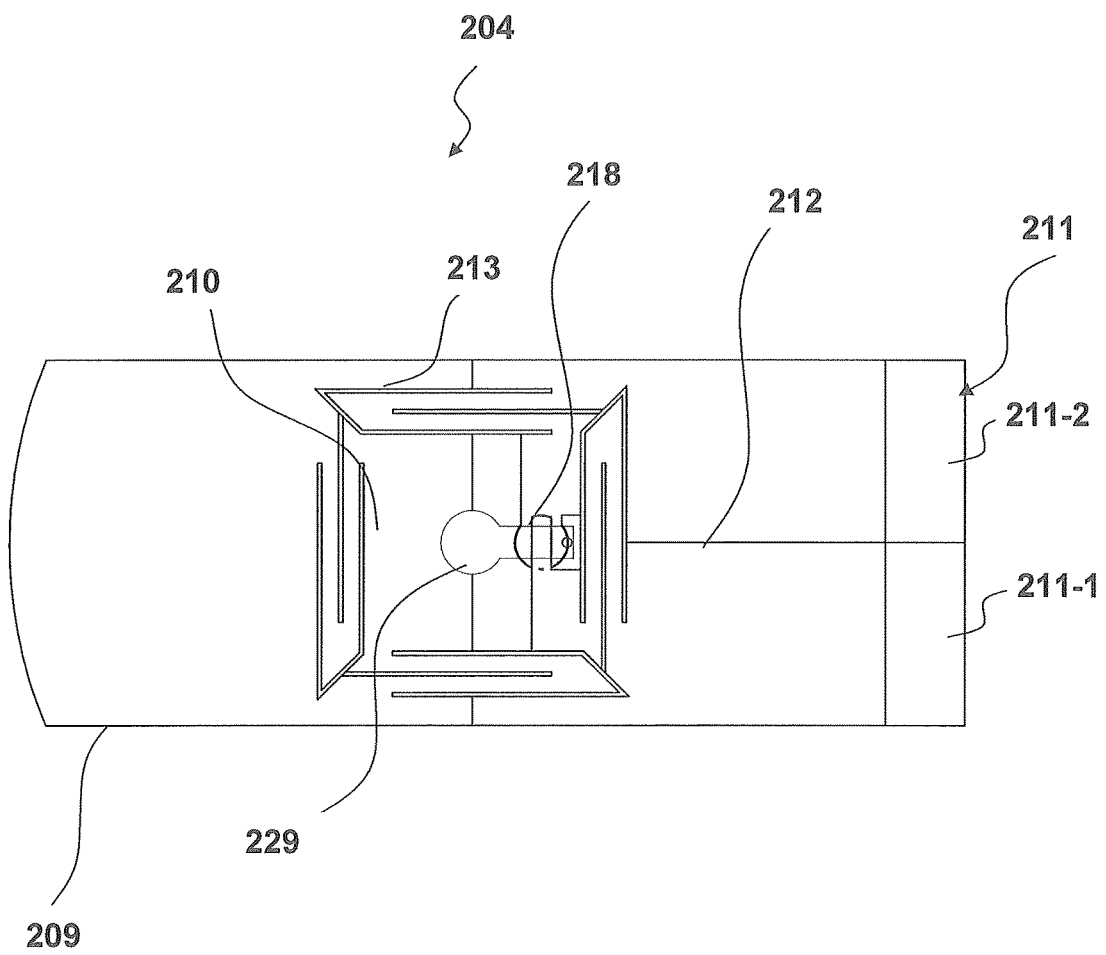
FIG. 15 is a plan view of the biosensor pertaining to Embodiment 2 of the present invention.

FIG. 15 shows the configuration of a biosensor 204 pertaining to Embodiment 2. The biosensor 204 differs from the biosensor in Embodiment 1 above in that a cutout 213 is provided so as to surround the four sides of a detector 210.

In the following description, portions having the same configuration and function as in the above embodiment will be numbered the same and will not be described again.

2.1 Biosensor

2.1.1 Configuration of Biosensor

The biosensor 204 pertaining to this embodiment is similar to the biosensor in Embodiment 1 in that ten biosensors, for example, are stacked and held for use in the sensor installation component 5 of the measurement device 100. The biosensors 204 are installed so that they can be automatically fed out one at a time to the position shown in FIG. 17.

As shown in FIG. 15, the biosensor 204 comprises a rectangular element substrate 209, a square detector 210 provided to the element substrate 209, a connection terminal 211 provided to an end in the long-side direction of the element substrate 209, and a continuity path 212 that connects the connection terminal 211 and the detector 210.

The element substrate 209 further has a cutout 213 formed so as to surround the four sides of the detector 210. The cutout 213 is disposed along the four sides of the detector 210, and each side is formed in a fork shape. Forming the cutout 213 in this shape allows the detector 210 to be uniformly lifted up with respect to the element substrate 209 no matter which part of detector 210 receives the contact pressure of the finger.

The connection terminal 211 has, for example, two or more detecting electrodes disposed for detecting a component of blood (the specimen). The detecting electrodes include a pair of electrodes consisting of a working electrode 211-1 and a counter electrode 211-2. The connection terminal 211 is electrically connected to a controller (not shown) provided inside the main case 1 of the measurement device 100.

Figure 16A:
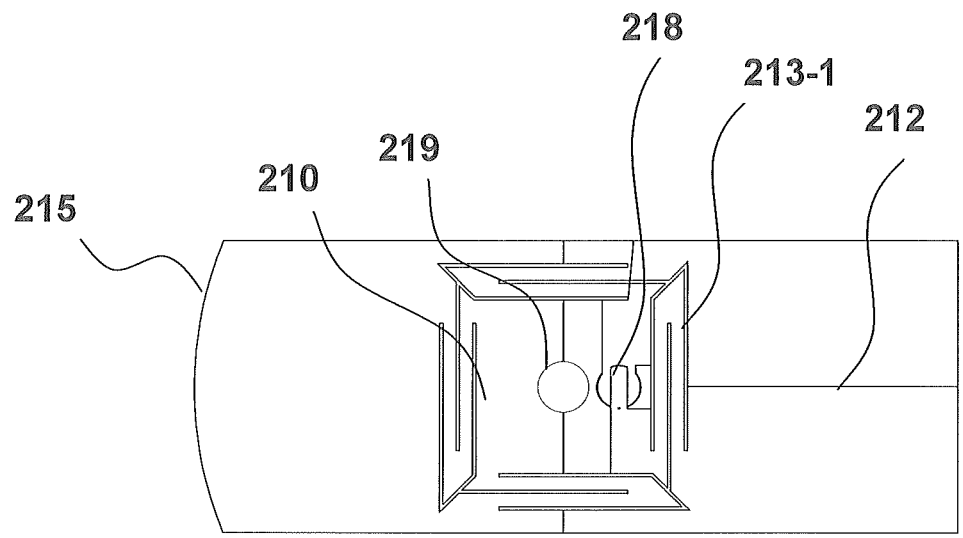
FIG. 16A is a plan view of part of the biosensor.
Figure 16B:
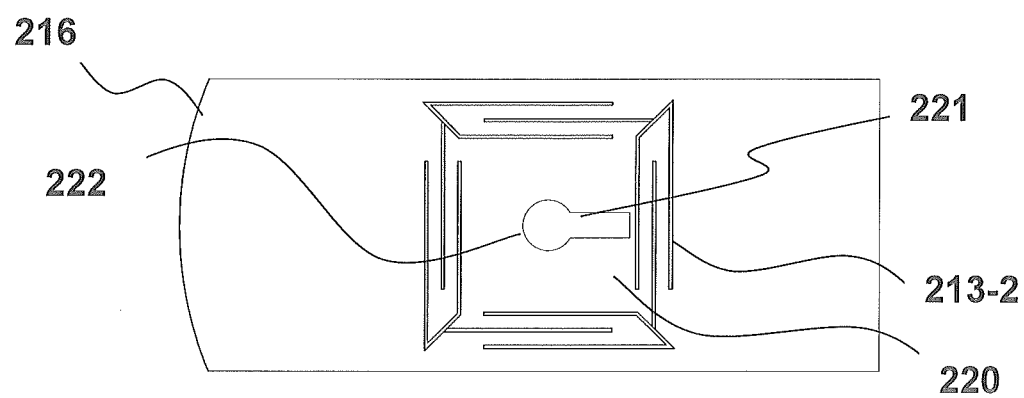
FIG. 16B is a plan view of part of the biosensor.
Figure 16C:
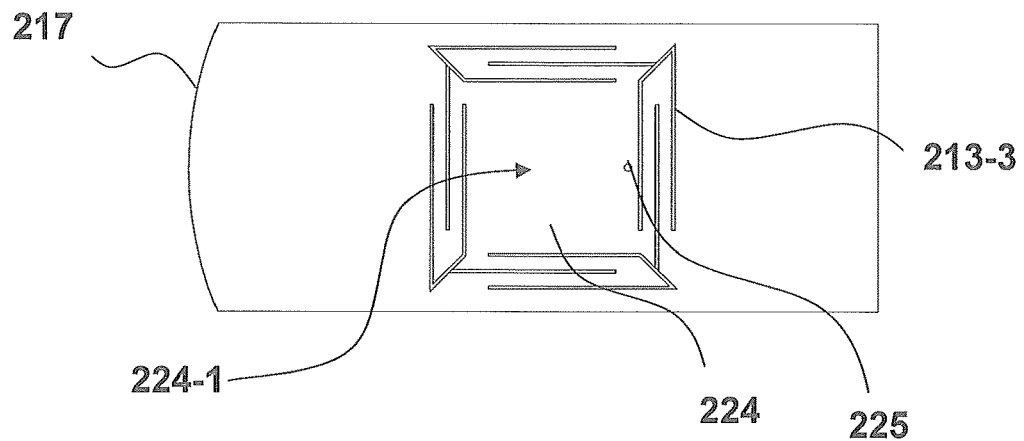
FIG. 16C is a plan view of part of the biosensor.

The biosensor 204 is constituted by laminating the three plates shown in FIGS. 16A to 16C. As shown in these drawings, the element substrate 209 of the biosensor 204 is constituted by laminating a rectangular lower plate 215 (FIG. 16A), a rectangular middle plate 216 provided over the lower plate 215 (FIG. 16B), and a rectangular upper plate 217 provided over the middle plate 216 (FIG. 16C), in that order from bottom to top.

The lower plate 215 includes a cutout 213-1 having substantially the same shape as the cutout 213, an elliptical reaction component 218 provided on the inside of the cutout 213-1, the continuity path 212, and the connection terminal 211. The detector 210 provided with the reaction component 218 is square in shape as mentioned above, and a circular puncture through-component 219 constituting part of a puncture component 229 (FIG. 15) is provided in the approximate center of the square detector 210.

The reaction component 218 is coated with a reagent for detecting the blood glucose level, for example. When blood is deposited on this reagent, a response current is produced by a redox reaction, which is a signal from the biosensor 204 in the reaction component 218. This response current is transmitted through the continuity path 212 and the connection terminal 211 to the measurement device 100. With the measurement device 100, the response current is converted into voltage. This voltage value is then converted into a specific digital value by A/D conversion, and is inputted to the controller. The controller measures blood concentration data, such as the hematocrit concentration or the glucose concentration (indicating the blood glucose level), on the basis of the digital value. After this, the information is displayed on the display component 2 in the same manner as in Embodiment 1.

Next, the middle plate 216 shown in FIG. 16B is provided with a cutout 213-2 that has substantially the same size and shape as the cutout 213. Also, a spacer 220 of substantially the same size as the detector 210 is formed on the inside of the cutout 213-2. A specimen supply route 221 is formed in the spacer 220. As shown in FIG. 16B, the specimen supply route 221 is comprised of a puncture through-hole 222 at a location corresponding to the puncture through-component 219 of the lower plate 215, and a narrow groove 223 that communicates with the puncture through-hole 222 and the reaction component 218 of the lower plate 215. The puncture through-hole 222 constitutes part of the puncture component 229 (FIG. 15).

The upper plate 217 shown in FIG. 16C is provided with a cutout 313-3 that has substantially the same size and shape as the cutouts 213-1 and 213-2. A cover 224 of substantially the same size as the detector 210 and the spacer 220 is formed on the inside of the cutout 213-3. The cover 224 has an air hole 225 formed so as to communicate with the narrow groove 223 of the spacer 220 in the middle plate 216 on the opposite side portion from the puncture through-hole 222. A non-through-component 224-1 is formed in the portion of the cover 224 of the upper plate 217 corresponding to the puncture through-component 219 of the lower plate 215 and the puncture through-hole 222 of the middle plate 216. The needle 7 shown in FIG. 17B punctures this non-through-component 224-1.

The lower plate 215, middle plate 216, and upper plate 217 shown in FIGS. 16A to 16C, respectively, are laminated in that order from bottom to top to form the biosensor 204 shown in FIG. 15.

2.1.2 Operation of Biosensor

Figure 17A:
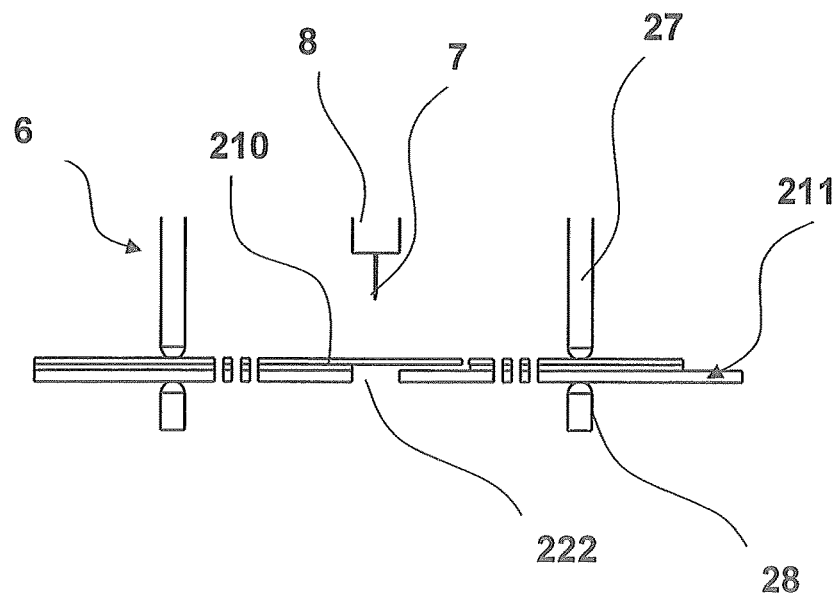
FIG. 17A is a cross section of the main components in a state in which the biosensor pertaining to Embodiment 2 has been placed in a measurement device.
Figure 17B:
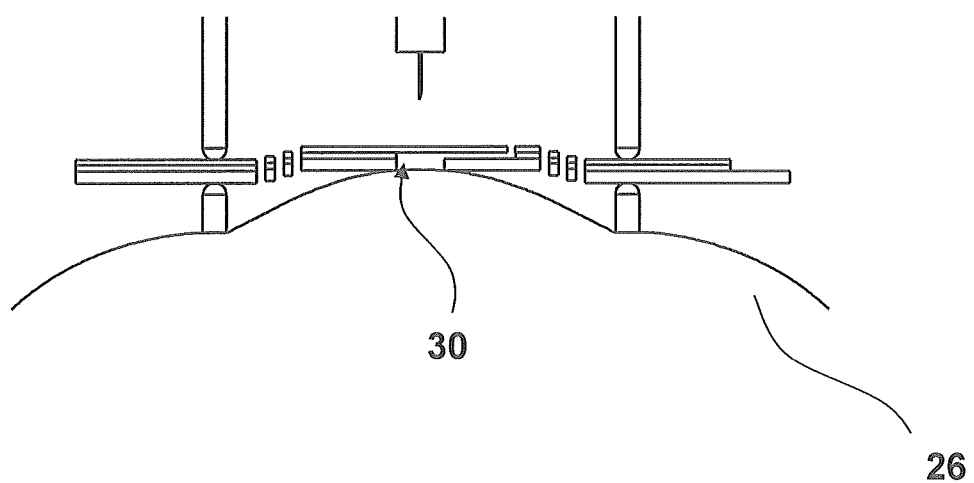
FIG. 17B is a cross section of the main components of the biosensor and the measurement device during the puncture operation.

When the blood glucose level is measured with the measurement device 100 shown in FIG. 1, as shown in FIG. 17A, the upper face of the biosensor 204 is pressed by an upper cylinder 27, which is the negative pressure formation component 6 and surrounds the portion corresponding to the detector 210 outside the cutout 213. The lower face of the biosensor 204 is also pressed by a lower cylinder 28, which is the negative pressure formation component 6 and surrounds the detector 210 outside the cutout 213, as shown in FIG. 17A. Next, the finger 26 of the user is pressed underneath the biosensor 204, which is in the sensor installation component 5 of the measurement device 100, as shown in FIG. 17B. In this state negative pressure is generated by the negative pressure formation component 6 and part of the finger 26 bulges upward as shown in FIG. 17B.

Here, when the finger 26 is snugly against the biosensor 204 and pressure is exerted on the biosensor 204, the portion of the biosensor 204 corresponding to the detector 210 is lifted upward according to the bulging of the finger. With the circular cutout in the biosensor 4 in Embodiment 1 above, the structure is such that pressure is released using a single support point, so the sensor ends up being bent far by the bulging of the finger if the support point is close to the puncture component. In contrast, with this embodiment, since cutouts are provided on all four sides, the contact pressure can be released uniformly in multiple directions, so the sensor is not bent very far.

When the needle 7 is moved downward by the needle movement component 8 in this state, the needle 7 goes through the puncture component 229 and punctures the finger 26. Then, when the needle 7 is moved upward by the needle movement component 8, blood flows out of the finger 26. This blood is deposited on the blood guide 30 of the biosensor 204 by the force of the negative pressure. The blood is then supplied through the specimen supply route 221 to the reaction component 218, the blood glucose component detected by the reaction component 218 is informed through the continuity path 212 and the connection terminal 211 to the controller (not shown) provided inside the main case 1 in FIG. 1, where the blood glucose level is calculated. After this, the blood glucose level is displayed as a measurement value on the display component 2.

2.2 Features of Biosensor

With the biosensor 204 pertaining to this embodiment, the cutout 213 is provided on all four sides so as to surround the detector 210, and the detector 210 is formed so that when it receives the contact pressure of the finger, it is lifted up (that is, moves away) uniformly, so contact pressure exerted by the finger can be released uniformly. Consequently, the sensor is not bent very much by the bulging up of the finger. As a result, contact pressure of the finger on the biosensor 204 can be suitably released and puncture can be carried out properly, allowing for better reliability of the measurement result.

2.3 Modification Example

Figure 18:
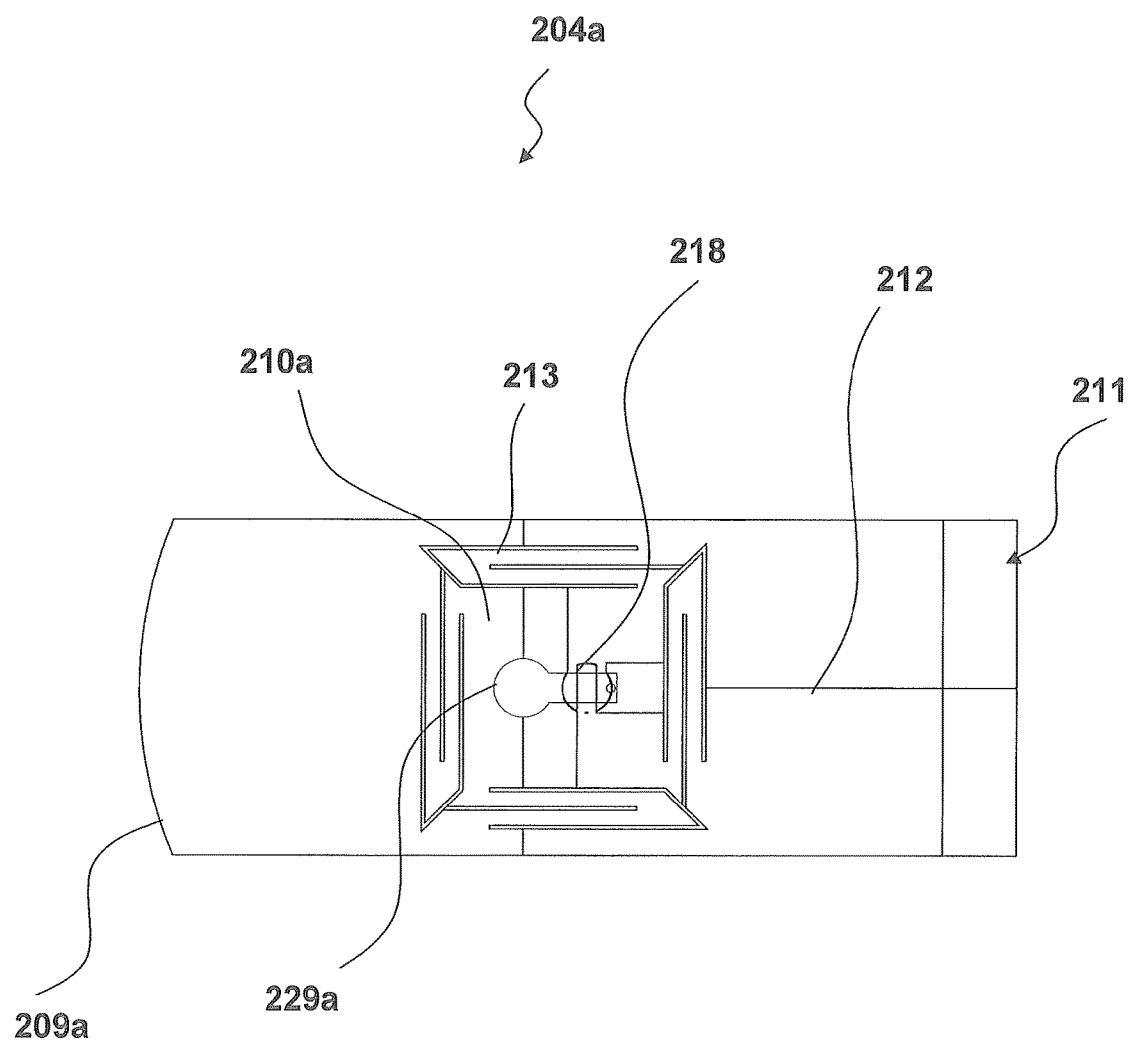
FIG. 18 is a plan view of the biosensor pertaining to a modification example of Embodiment 2.

FIG. 18 shows a biosensor 204a in a modification example of Embodiment 2 above. This modification example differs from Embodiment 2 above in that a puncture component 229a formed on an element substrate 209a is offset by a specific distance from the approximate center of a square detector 210a.

Figure 19A:
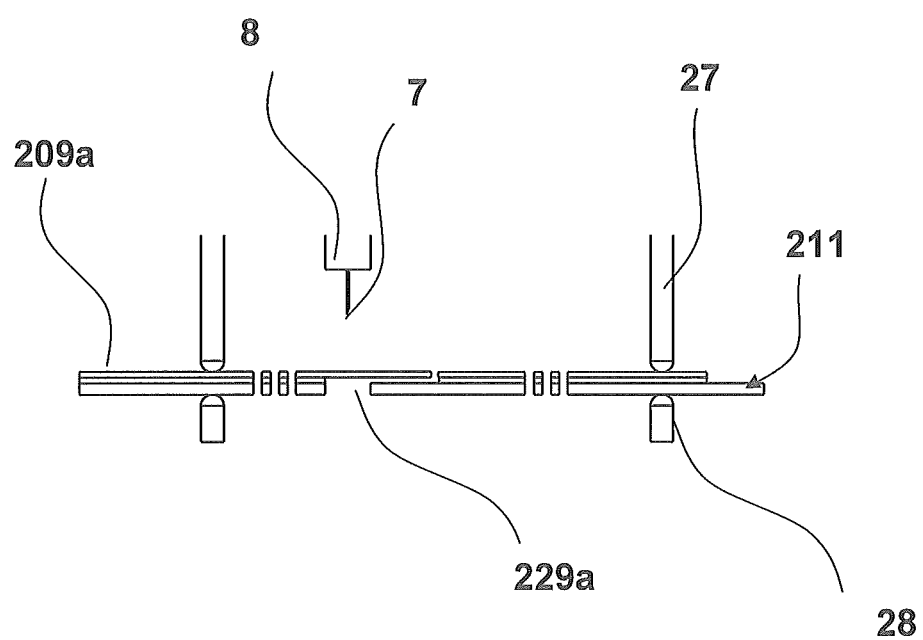
FIG. 19A is a cross section of the main components in a state in which the biosensor pertaining to this modification example has been placed in a measurement device.
Figure 19B:
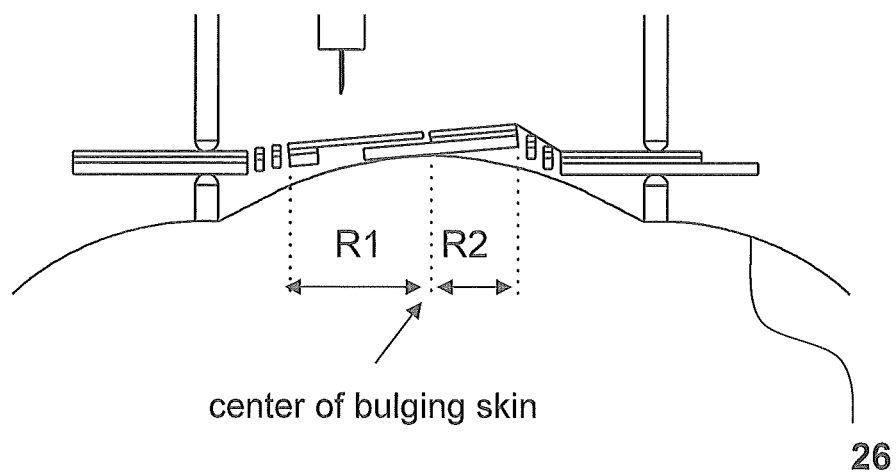
FIG. 19B is a cross section of the main components of the biosensor and the measurement device during the puncture operation.

With this configuration, the puncture component 229a is offset from the center of the bulging of the finger. In this case, as shown in FIG. 19B, the amount of offset from the above-mentioned center position of the puncture component is preferably set by varying the ratio between the distances R1 and R2 between the outer periphery of the detector and the center of the bulging of the finger. This is because the blood will be introduced more readily when the distance between the puncture component and the finger is as short as possible. Also, the amount of bulging of the finger varies greatly from one individual to the next depending on the hardness or softness of the skin and so forth, making it difficult to adjust the puncture depth, but the farther the puncture component is from the center of bulging of the finger, the less the sensor is able to move, which makes adjustment of the puncture depth easier.

3. Embodiment 3

FIG. 20 shows the configuration of a biosensor 304 pertaining to Embodiment 3. The biosensor 304 differs from the one in Embodiment 2 above in that a cutout 313 is formed so that when contact pressure is exerted on a detector 310, the detector is easily lifted up in the lengthwise direction of the biosensor 304, that is, in the forward and backward direction.

In the following description, those portions having the same configuration and function as in the above embodiments will not be described again in detail.

3.1 Biosensor

3.1.1 Configuration of Biosensor

The biosensor 304 pertaining to this embodiment is similar to the biosensor in Embodiment 2 in that ten biosensors, for example, are stacked and held for use in the sensor installation component 5 of the measurement device 100 shown in FIG. 1. The biosensors 304 are installed so that they can be automatically fed out one at a time.

Figure 20A:
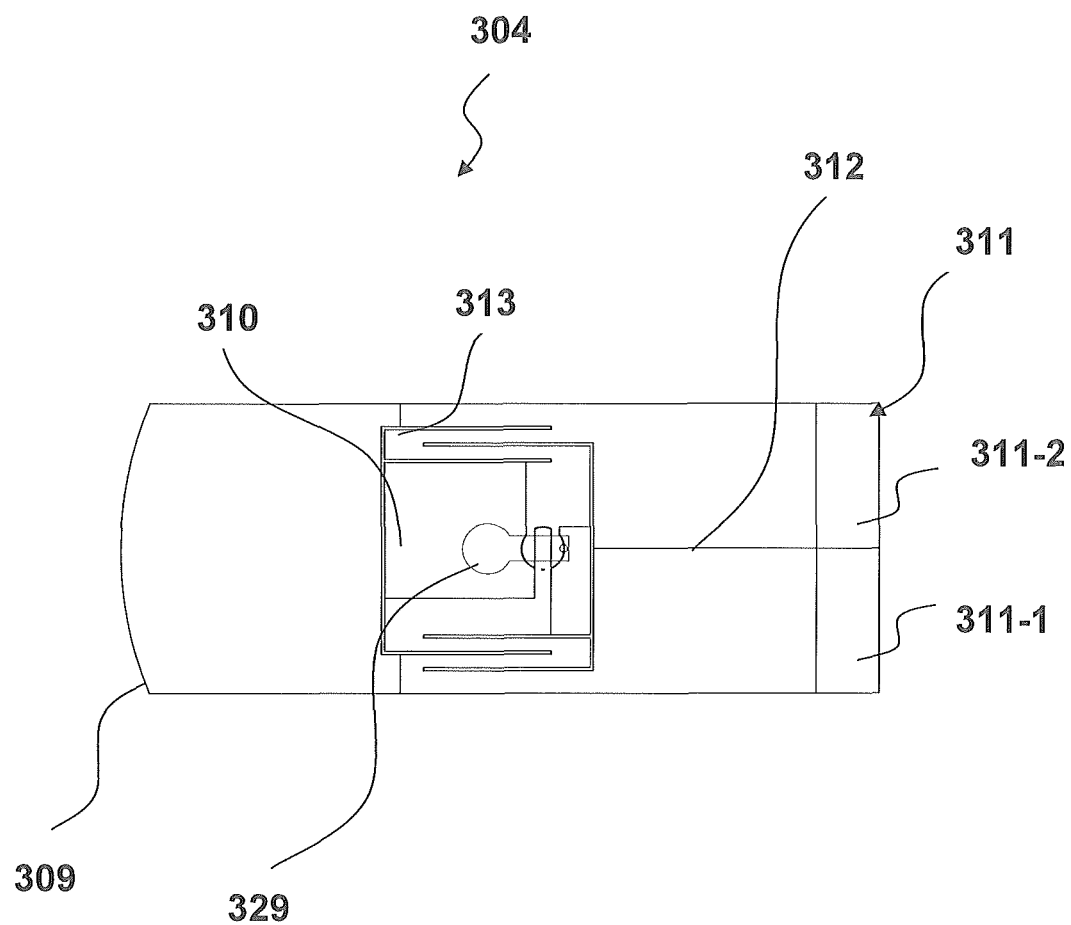
FIG. 20A is a plan view of the biosensor pertaining to Embodiment 3 of the present invention.

As shown in FIG. 20A, the biosensor 304 comprises a rectangular element substrate 309, a square detector 310 provided to the element substrate 309, a connection terminal 311 provided to an end in the long-side direction of the element substrate 309, and a continuity path 312 that connects the connection terminal 311 and the detector 310.

Figure 20B:
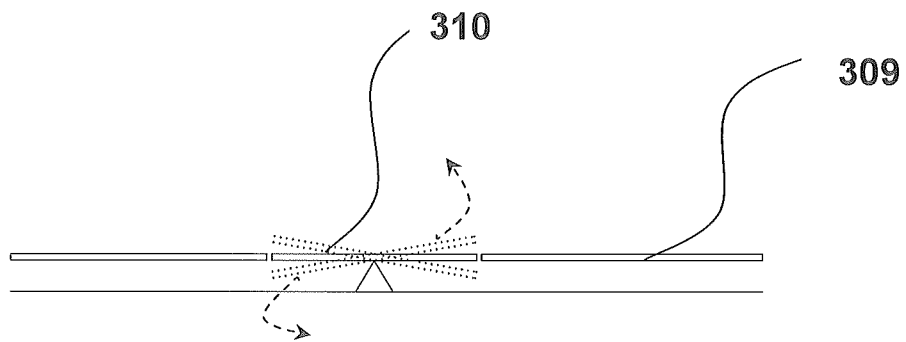
FIG. 20B is a cross section of the operation of the biosensor.

As shown in FIG. 20A, the element substrate 309 further has the cutout 313 formed so as to surround the detector 310. The cutout 313 has two sides in the short-side direction (that is, the width direction) of the element substrate 309, each of which is formed in a fork shape, and other two sides in the long-side direction (that is, the forward and backward direction), each of which is a linear shape. Forming the cutout 213 in this shape allows the detector 310 to be easily lifted up in the long-side direction of the biosensor 304 upon receiving the contact pressure of the finger, as shown in FIG. 20B.

The connection terminal 311 comprises two detecting electrodes for detecting a component of blood (the specimen), and includes a pair of electrodes consisting of a working electrode 311-1 and a counter electrode 311-2. The connection terminal 311 is electrically connected to a controller (not shown) provided inside the main case 1 of the measurement device 100.

The rest of the configuration is the same as in Embodiments 1 and 2 above and will not be described again.

3.1.2 Operation of Biosensor

When the blood glucose level is measured with the measurement device 100 shown in FIG. 1, the upper cylinder 27 (FIG. 17A), which is the negative pressure formation component 6, is pressed against the upper face of the biosensor 304 on the outside of the cutouts 313 just as in Embodiment 2. The lower cylinder 28 (FIG. 17A), which is the negative pressure formation component 6, is also pressed against the lower face of the biosensor 304 on the outside of the cutouts 313. Then, the finger 26 of the user is pressed underneath the biosensor 304, which is in the sensor installation component 5 of the measurement device 100. Negative pressure is generated by the negative pressure formation component 6 in this state, causing part of the finger 26 to bulge up.

Here, when the finger 26 is snugly against the biosensor 304 and pressure is exerted on the biosensor 304, the detector 310 is lifted upward in either the forward or backward direction of the biosensor 304 as shown in FIG. 20B, according to the bulging of the finger.

In this state, the puncture operation is carried out, blood is collected, and the blood glucose level is calculated in the same manner as in Embodiment 2.

3.2 Features of Biosensor

With the biosensor 304 pertaining to this embodiment, as shown in FIG. 20A, the cutout 313 is formed so as to surround the detector 310, and the detector 310 is easily lifted up (that is, moved away) with respect to the element substrate 309 in the long-side direction of the biosensor 304, that is, in the backward and forward direction. Consequently, contact pressure of the finger on the biosensor 304 can be suitably released and puncture can be carried out properly, allowing for better reliability of the measurement result.

3.3 Modification Example

Figure 21A:
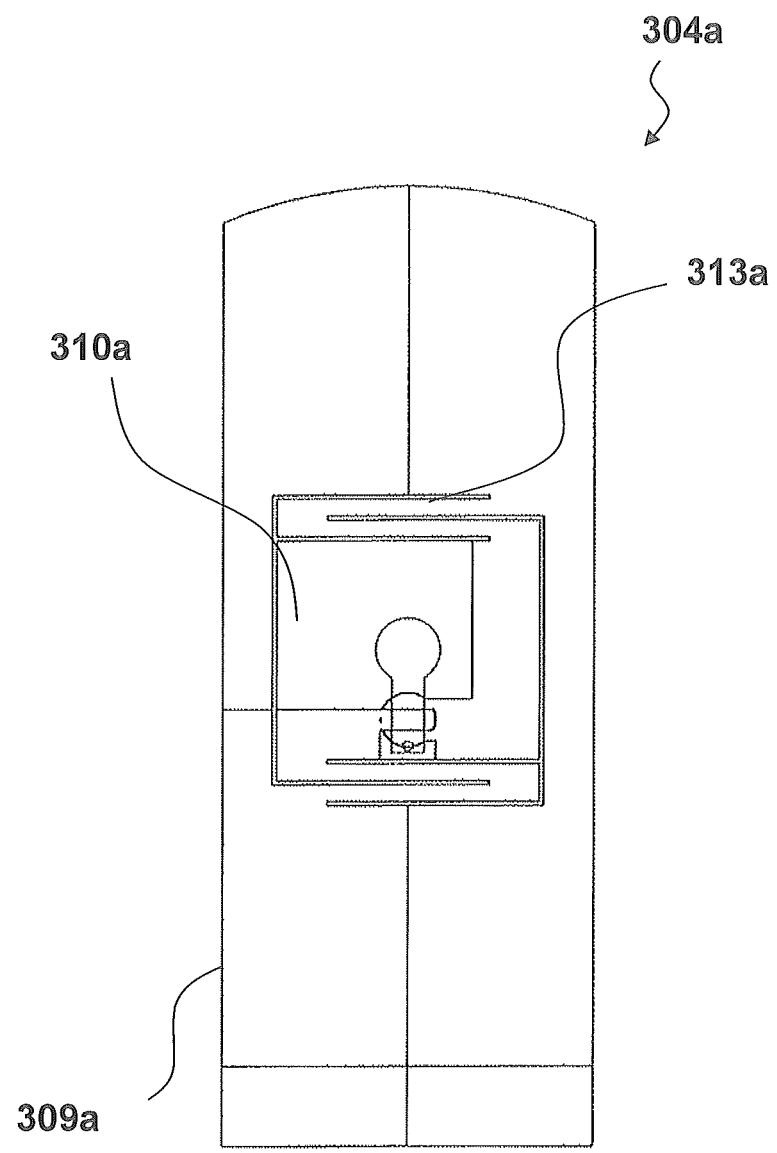
FIG. 21A is a plan view of the biosensor pertaining to a modification example of Embodiment 3.
Figure 21B:
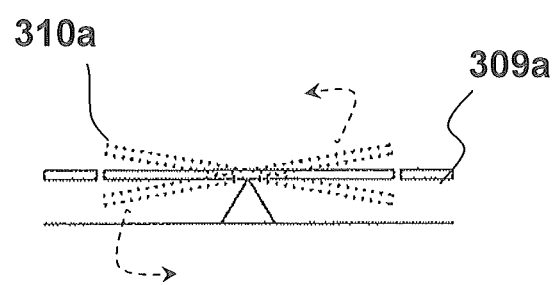
FIG. 21B is a cross section of the operation of the biosensor.

FIG. 21A shows a biosensor 304a in a modification example of Embodiment 3 above. This modification example differs from Embodiment 2 above in that a cutout 313a is formed so that when contact pressure is exerted on a detector 310a formed on a element substrate 309a, the detector is easily lifted up (that is, moved away) in the short-side direction (that is, the width direction) of the biosensor 304a, as shown in FIG. 21B.

With this configuration, just as in Embodiment 3 above, contact pressure of the finger on the biosensor 304a can be suitably released and puncture can be carried out properly, allowing for better reliability of the measurement result.

4. Embodiment 4

Figure 22:
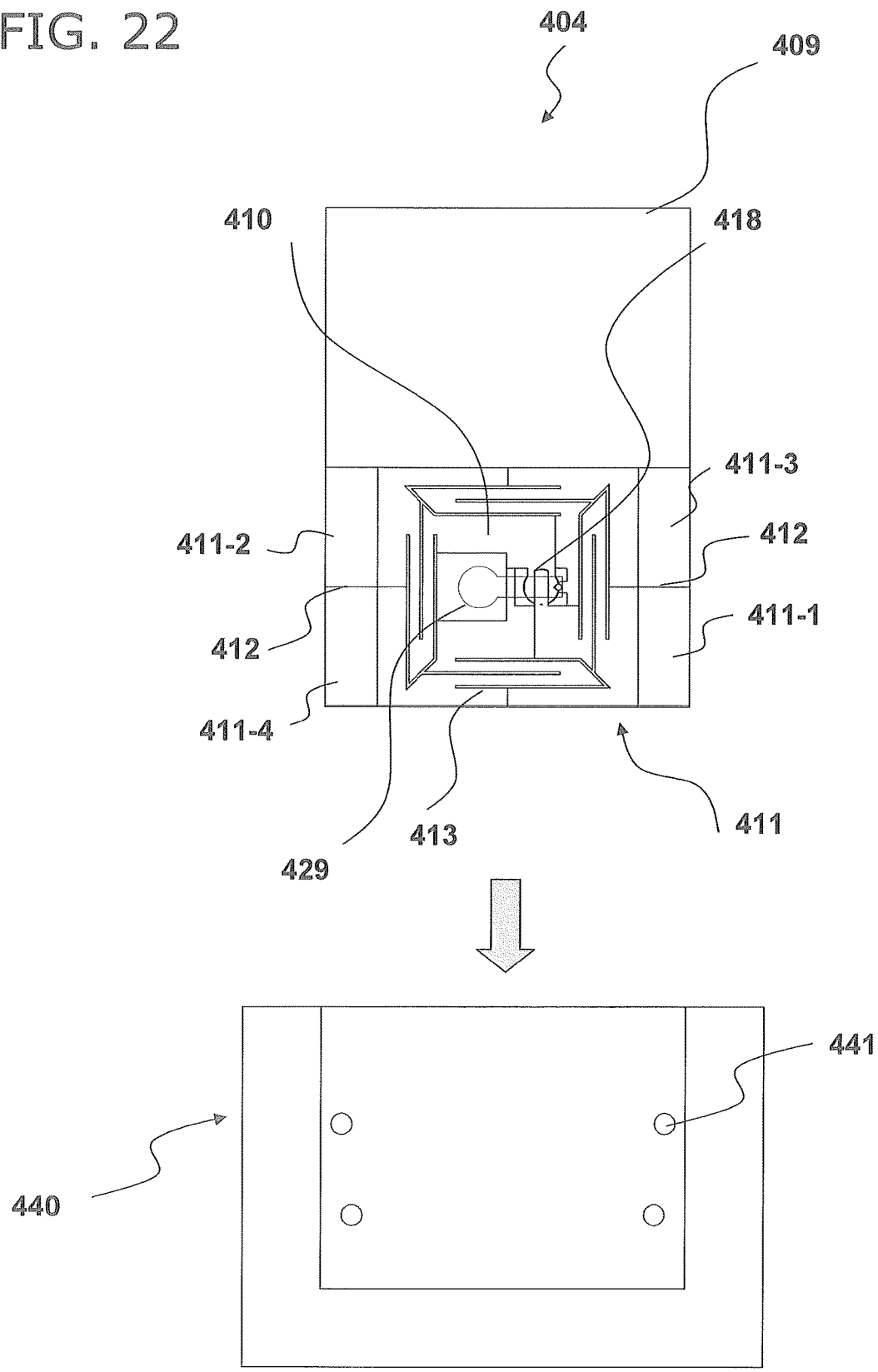
FIG. 22 is a plan view of the biosensor and sensor insertion component pertaining to Embodiment 4 of the present invention.

FIG. 22 shows the configuration of a biosensor 404 pertaining to Embodiment 4. The biosensor 404 differs from the ones in the above embodiments in that a four-pole connection terminal 411 is provided on the left and right sides in the insertion direction of the sensor with respect to the measurement device 100, that is, the short-side direction of the biosensor.

In the following description, those portions having the same configuration and function as in the above embodiments will not be described again in detail.

4.1 Biosensor

4.1.1 Configuration of Biosensor

As shown in FIG. 22, the biosensor 404 comprises a rectangular element substrate 409, a square detector 410 provided to the element substrate 409, a connection terminal 411 provided on both sides of the short-side direction (that is, the width direction) at an end of the element substrate 409, and a continuity path 412 that connects the connection terminal 411 and the detector 410.

The element substrate 409 further has the cutout 413 formed so as to surround the detector 410 just as in Embodiment 2 above. The cutout 413 is disposed along the four sides of the detector 410, and each side is formed in a fork shape. A puncture component 429 and a reaction component 418 that is coated with a reagent for detecting the blood glucose level are formed on the detector 410.

Figure 23A:
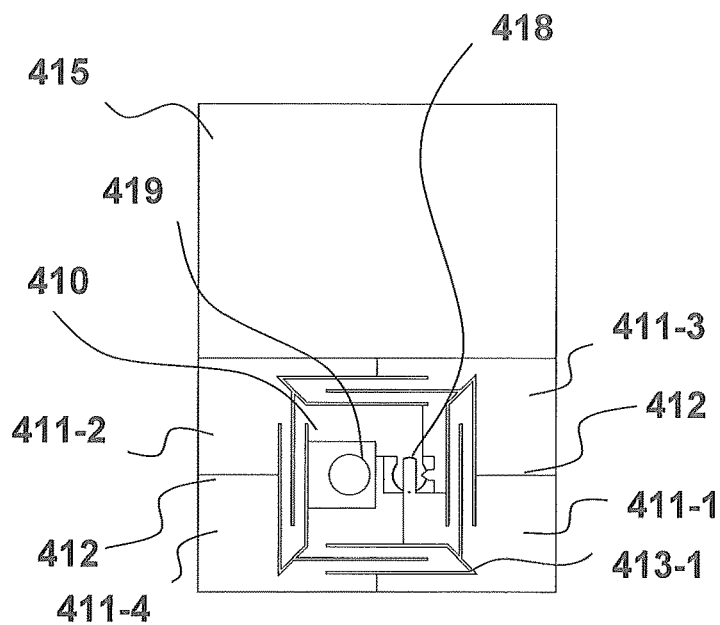
FIG. 23A is a plan view of part of the biosensor.
Figure 23B:
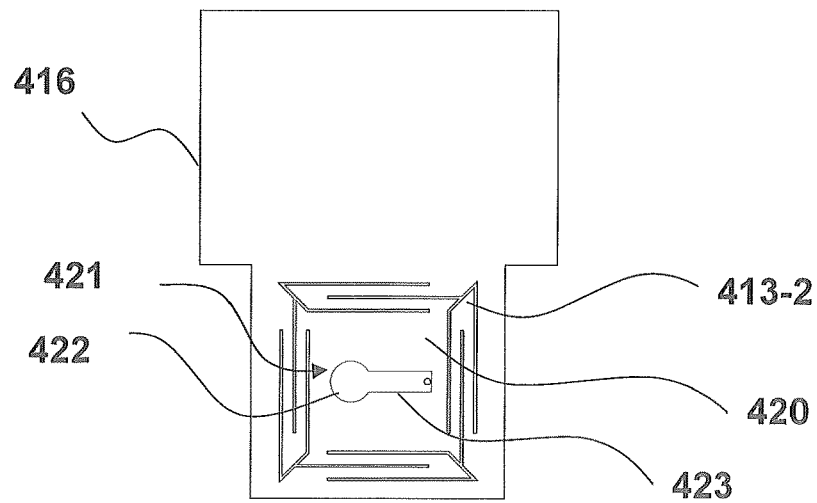
FIG. 23B is a plan view of part of the biosensor.
Figure 23C:
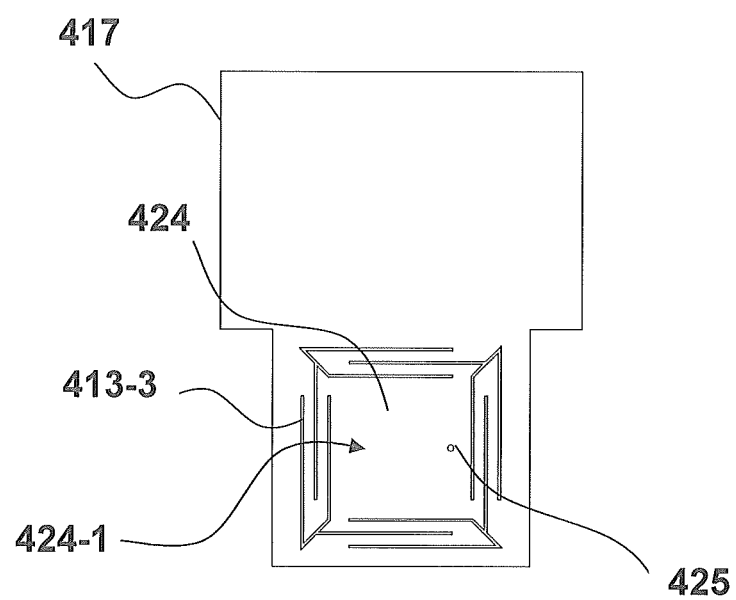
FIG. 23C is a plan view of part of the biosensor.

The biosensor 404 is constituted by laminating three plates as shown in FIGS. 23A to 23C. As shown in these drawings, the element substrate 409 constituting the biosensor 404 is constituted by laminating a rectangular lower plate 415 (FIG. 23A), a middle plate 416 provided over the lower plate 415 (FIG. 23B), and an upper plate 417 provided over the middle plate 416 (FIG. 23C), in that order from bottom to top. The lower plate 415 includes a cutout 413-1 having substantially the same shape as the cutout 413, the reaction component 418 provided on the inside of the cutout 413-1, the continuity path 412, and the connection terminal 411. The detector 410 provided with the reaction component 418 is square in shape as mentioned above, and a circular puncture through-component 419 constituting part of the puncture component 429 (FIG. 22) is provided at a position that is slightly offset from the approximate center of the square detector 410.

The connection terminal 411 is a detecting electrode for detecting a component of blood (the specimen), and as shown in FIGS. 22 and 23A, includes a working electrode 411-1, a counter electrode 411-2, a detecting electrode 411-3, and an Hct measurement electrode 411-4. The detecting electrode is used to detect whether or not blood has been supplied to the reaction component 418. The Hct electrode is used to measure the hematocrit value in blood. The connection terminal 411 is electrically connected to a controller (not shown) provided inside the main case 1 of the measurement device 100 (FIG. 1).

The reaction component 418 is coated with a reagent for detecting the blood glucose level, for example, and the blood glucose level is measured in the same manner as in the above embodiments by depositing blood on the reagent.

As shown in FIG. 23B, the middle plate 416 has a rectangular shape, from which is missing the portion corresponding to the connection terminal 411 of the lower plate 415. The middle plate 416 is provided with a cutout 413-2 of substantially the same size and shape as the cutout 413. Also, a spacer 420 of substantially the same size as the detector 410 is formed on the inside of the cutout 413-2. As shown in FIG. 23B, the specimen supply route 421 is comprised of a puncture through-hole 422 corresponding to the puncture through-component 419 of the lower plate 415, and a narrow groove 423 that communicates with the puncture through-hole 422 and the reaction component 418 of the lower plate 415. The puncture through-hole 422 constitutes part of the puncture component 429 (FIG. 22).

As shown in FIG. 23C, the upper plate 417 has a rectangular shape, from which is missing the portion corresponding to the connection terminal 411 of the lower plate 415. The upper plate 417 is provided with a cutout 413-3 of substantially the same size and shape as the cutouts 413-1 and 413-2. A cover 424 of substantially the same size as the spacer 420 and the detector 410 is formed on the inside of the cutout 413-3. The cover 424 has an air hole 425 formed so as to communicate with the portion of the narrow groove 423 of the spacer 420 in the middle plate 416 that is on the opposite side from the puncture through-hole 422. A non-through-component 424-1 is formed in the portion of the cover 424 of the upper plate 417 corresponding to the puncture through-component 419 of the lower plate 415 or the puncture through-hole 422 of the middle plate 416. The non-through-component 424-1 is punctured by a needle. The non-through-component 424-1 constitutes part of the puncture component 429 (FIG. 22).

The lower plate 415, middle plate 416, and upper plate 417 shown in FIGS. 23A to 23C, respectively, are laminated in that order from bottom to top to form the biosensor 404 shown in FIG. 22.

4.1.2 Operation of Biosensor

As shown in FIG. 22, in this embodiment, connector pins 441 (an example of a connection component) that connect the detecting electrodes of the connection terminal 411 of the biosensor 404 are provided to a sensor insertion component 440 provided to the sensor installation component 5 of the measurement device 100 (FIG. 1). As shown in FIG. 22, the connector pins 441 are arranged in pairs spaced a specific distance apart in the width direction of the sensor, with the spacing wider for the pair that is closer in the sensor insertion direction. Arranging the connector pins 441 in this way prevents the connector pins 441 from scratching the connection terminal 411 during sensor insertion.

When the biosensor 404 is properly inserted into the sensor insertion component 440, the working electrode 411-1, the counter electrode 411-2, the detecting electrode 411-3, and the Hct measurement electrode 411-4 are each connected to one of the connector pins 441. In this state, just as in the above embodiments, the blood glucose level is measured by depositing blood on the detector 410 of the biosensor 404.

4.2 Features of Biosensor

With the biosensor 404 pertaining to this embodiment, the connection terminal 411 is provided on both sides of the short-side direction at an end of the biosensor 404. Also, the connector pins 441 that connect to the working electrode 411-1, the counter electrode 411-2, the detecting electrode 411-3, and the Hct measurement electrode 411-4 of the connection terminal 411 of the biosensor 404 respectively are provided to the sensor insertion component 440 provided to the sensor installation component 5 of the measurement device 100 (FIG. 1). With this configuration, the biosensor 404 can be formed in a more compact size, particularly in the lengthwise direction.

Also, the connector pins 441 are formed with a wider spacing for the pair that is closer in the sensor insertion direction, which prevents the connector pins 441 from scratching the connection terminal 411 during sensor insertion.

4.3 Modification Example

Figure 24:
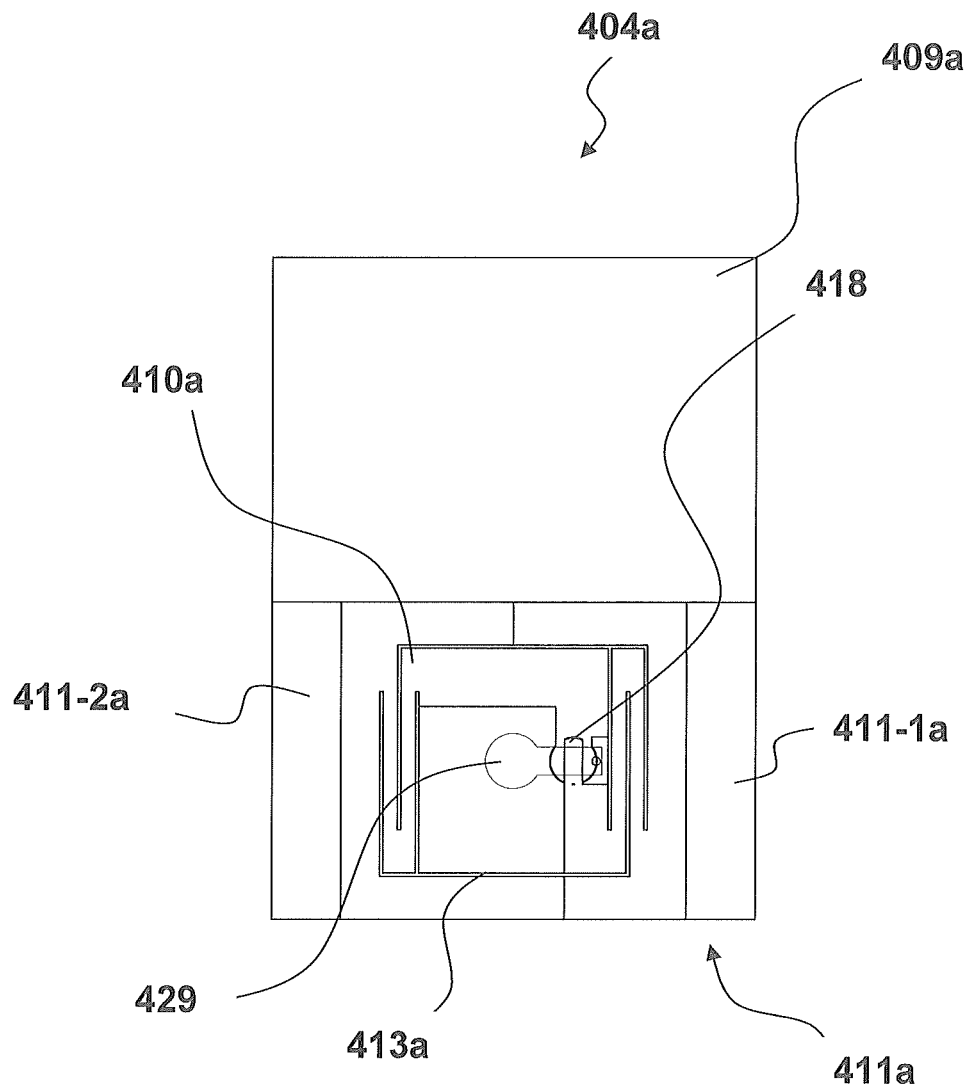
FIG. 24 is a plan view of the biosensor pertaining to a modification example of Embodiment 4.

FIG. 24 shows a biosensor 404a in a modification example of Embodiment 4 above. In this modification example, an element substrate 409a is formed so as to surround a detector 410a as shown in FIG. 24, and just as in Embodiment 3, the detector 410a is formed so that when finger contact pressure is exerted, the detector is easy to lift up (that is move away) in the lengthwise direction (that is, the backward and forward direction) of the biosensor 404a (FIG. 20B).

Figure 25A:
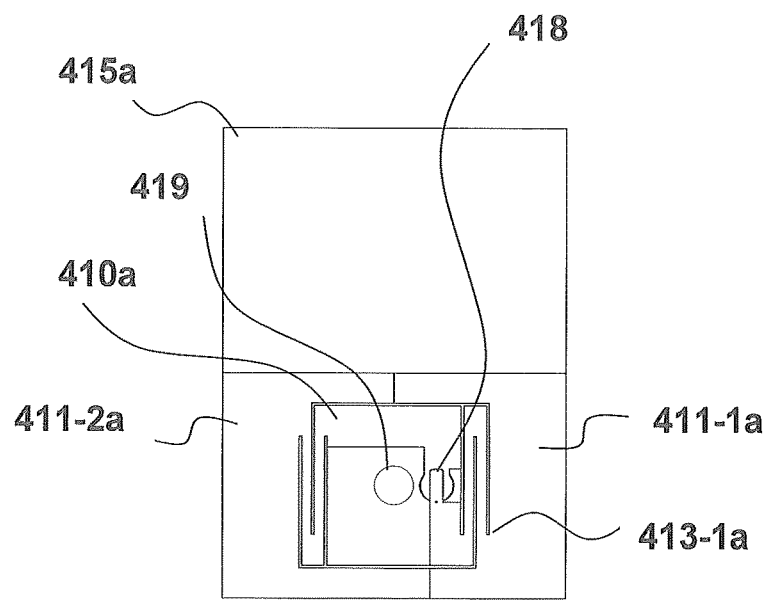
FIG. 25A is a plan view of part of the biosensor.
Figure 25B:
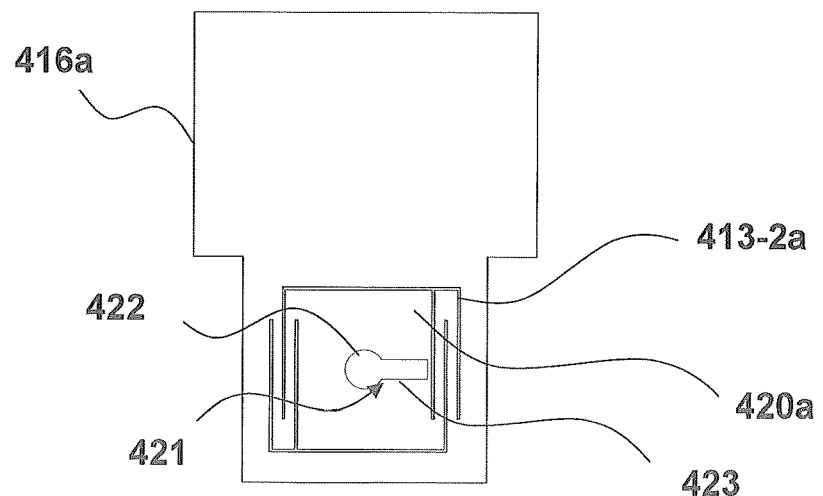
FIG. 25B is a plan view of part of the biosensor.
Figure 25C:
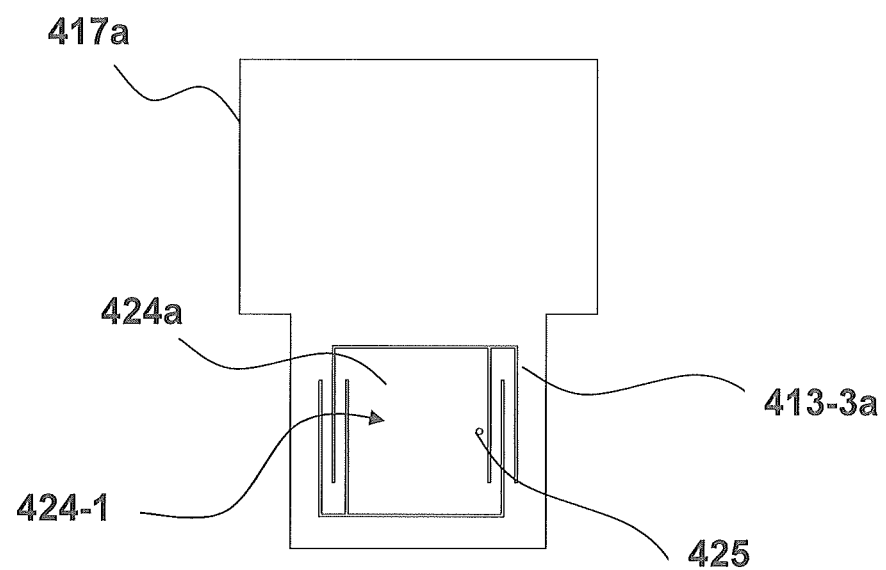
FIG. 25C is a plan view of part of the biosensor.

The biosensor 404a is constituted by laminating the three plates shown in FIGS. 25A to 25C. As shown in these drawings, an element substrate 409a of the biosensor 404a is constituted by laminating a rectangular lower plate 415a (FIG. 25A), a middle plate 416a provided over the lower plate 415a (FIG. 25B), and an upper plate 417a provided over the middle plate 416a (FIG. 25C), in that order from bottom to top. The lower plate 415a includes a cutout 413-1a having substantially the same shape as the cutout 413a, a reaction component 418 provided on the inside of the cutout 413-1a, a continuity path (not shown), and the connection terminal 411. The detector 410 provided with the reaction component 418 is square in shape as mentioned above, and a circular puncture through-component 419 constituting part of a puncture component 429 (FIG. 24) is provided in the approximate center of the square detector 410.

The connection terminal 411a is a detecting electrode for detecting a component of blood supplied to the supply route, and as shown in FIGS. 24 and 25A, comprises a working electrode 411-1a and a counter electrode 411-2a. The connection terminal 411a is electrically connected to a controller (not shown) provided inside the main case 1 of the measurement device 100.

The reaction component 418 is coated with a reagent for detecting the blood glucose level, for example. When blood is deposited on this reagent, the blood glucose level is measured in the same manner as in the above embodiments.

As shown in FIG. 25B, the middle plate 416 has a rectangular shape, from which is missing the portion corresponding to the connection terminal 411a of the lower plate 415a. The middle plate 416a is provided with a cutout 413-2a of substantially the same size and shape as the cutout 413. Also, a spacer 420a of substantially the same size as the detector 410a is formed on the inside of the cutout 413-2a. As shown in FIG. 25B, the specimen supply route 421 is comprised of a puncture through-hole 422 corresponding to the puncture through-component 419 of the lower plate 415a, and a narrow groove 423 that communicates with the puncture through-hole 422 and the reaction component 418 of the lower plate 415a. The puncture through-hole 422 constitutes part of the puncture component 429 (FIG. 22).

As shown in FIG. 25C, the upper plate 417a has a rectangular shape, from which is missing the portion corresponding to the connection terminal 411a of the lower plate 415a. The upper plate 417a is provided with a cutout 413-3a of substantially the same size and shape as the cutouts 413-1a and 413-2a. A cover 424a of substantially the same size as the spacer 420a and the detector 410a is formed on the inside of the cutout 413-3a. The cover 424a has an air hole 425 formed so as to communicate with the portion of the narrow groove 423 of the spacer 420a in the middle plate 416a that is on the opposite side from the puncture through-hole 422. A non-through-component 424-1 is formed in the portion of the cover 424a of the upper plate 417a corresponding to the puncture through-component 419 of the lower plate 415a and the puncture through-hole 422 of the middle plate 416a. The non-through-hole component 424-1 is punctured by a needle. The non-through-component 424-1 constitutes part of the puncture component 429 (FIG. 22).

The lower plate 415a, middle plate 416a, and upper plate 417a shown in FIGS. 25A to 25C, respectively, are laminated in that order from bottom to top to form the biosensor 404a shown in FIG. 24.

With the above configuration, the biosensor 404a can be formed in a compact size in the lengthwise direction, just as in Embodiment 4 above.

5. Embodiment 5

Figure 26:
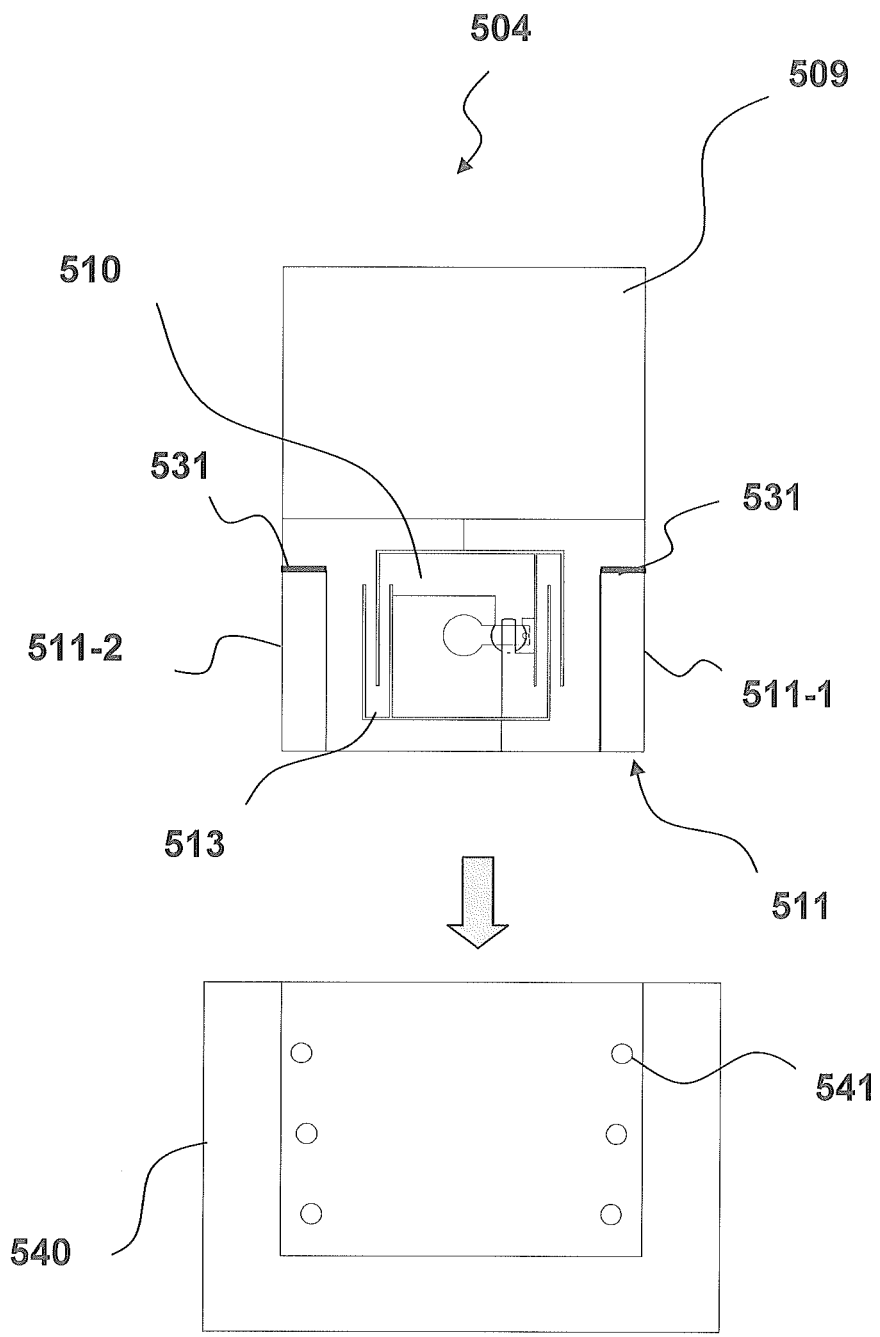
FIG. 26 is a plan view of the biosensor and sensor insertion component pertaining to Embodiment 5 of the present invention.

FIG. 26 shows the configuration of a biosensor 504 pertaining to Embodiment 5. This biosensor 504 has a configuration in which positioning of the biosensor 504 with respect to the measurement device 100 is performed by utilizing connector pins 541 that connect to connection terminals 511 of the biosensor 504 and that are formed on a sensor insertion component 540 provided to the sensor installation component 5 of the measurement device 100 (FIG. 1), and a biosensor (the type shown in FIG. 22 or 24, for example) provided with the connection terminals 511 on the left and right of the short-side direction of the biosensor 504, that is, the insertion direction of the sensor with respect to the measurement device 100.

In the following description, portions having the same configuration and function as in the above embodiments will not be described again.

5.1 Biosensor

5.1.1 Configuration of Biosensor

As shown in FIG. 26, the biosensor 504 comprises a rectangular element substrate 509, a square detector 510 provided to the element substrate 509, connection terminals 511 provided on both sides of the width direction of the sensor at an end of the element substrate 509, slits 531 provided at upper sides of the connection terminals 511 on the element substrate 509, that is, at the ends of the connection terminals 511 and on the opposite side of the biosensor 504 from the insertion direction, and a continuity path (not shown) that connects the connection terminals 511 and the detector 510. In this embodiment, the detector 510 and the cutout 513 may be in any form as long as the connection terminals 511 are provided on both sides of the short-side direction (width direction) of the sensor.

The connection terminals 511 are detecting electrodes for detecting a component of blood (the specimen), and comprise a working electrode 511-1 and a counter electrode 511-2. The connection terminals 511 are electrically connected to a controller (not shown) provided inside the main case 1 of the measurement device 100.

Just as in Embodiment 3, the biosensor 504 is formed by laminating a lower plate, a middle plate, and an upper plate in that order from bottom to top.

5.1.2 Operation of Biosensor

As shown in FIG. 26, in this embodiment, connector pins 541 (an example of a connection component) that connect to the connection terminals 511 of the biosensor 504 during sensor insertion are provided to the sensor insertion component 540 provided to the sensor installation component 5 of the measurement device 100 (FIG. 1). As shown in FIG. 26, the connector pins 541 are arranged in pairs spaced a specific distance apart on the left and right of the insertion direction of the biosensor 504. The spacing of the pairs of connector pins 541 increases toward the front in the sensor insertion direction, and narrows toward the rear. Arranging the connector pins 541 in this way prevents the connector pins 541 from scratching the connection terminals 511 during sensor insertion.

Figure 27A:
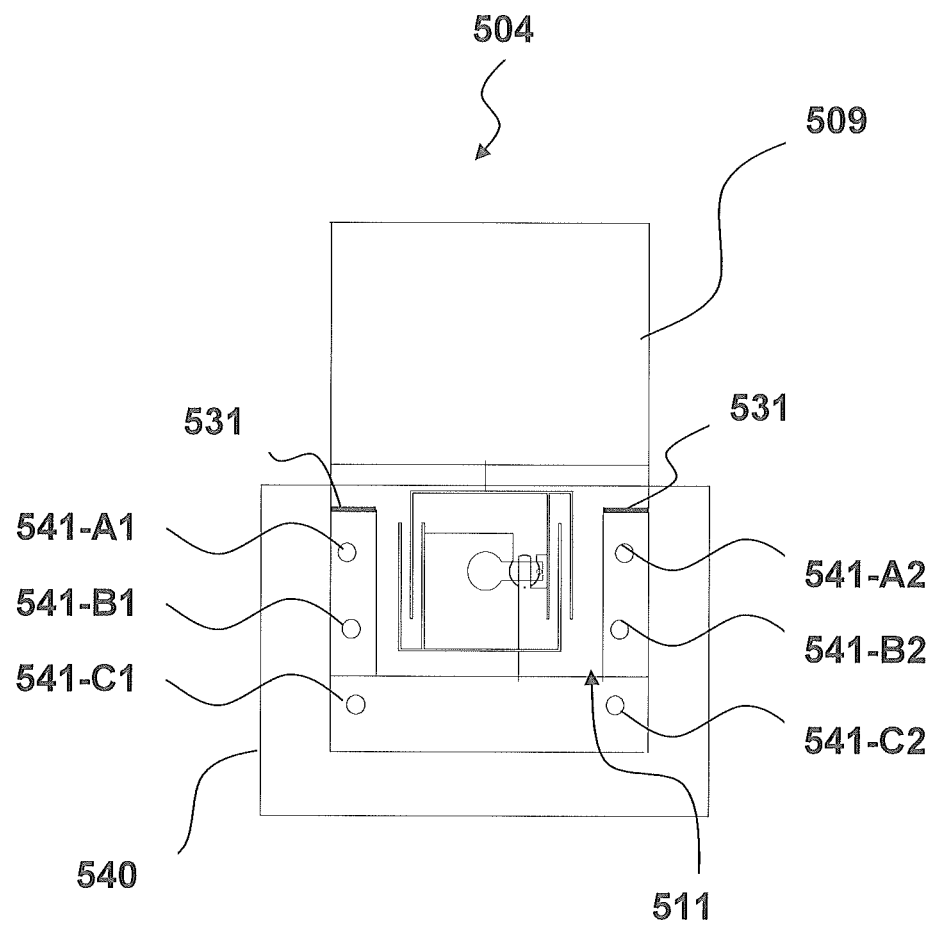
FIG. 27A is a plan view of a state in which the biosensor has been inserted into a sensor insertion component.
Figure 27B:
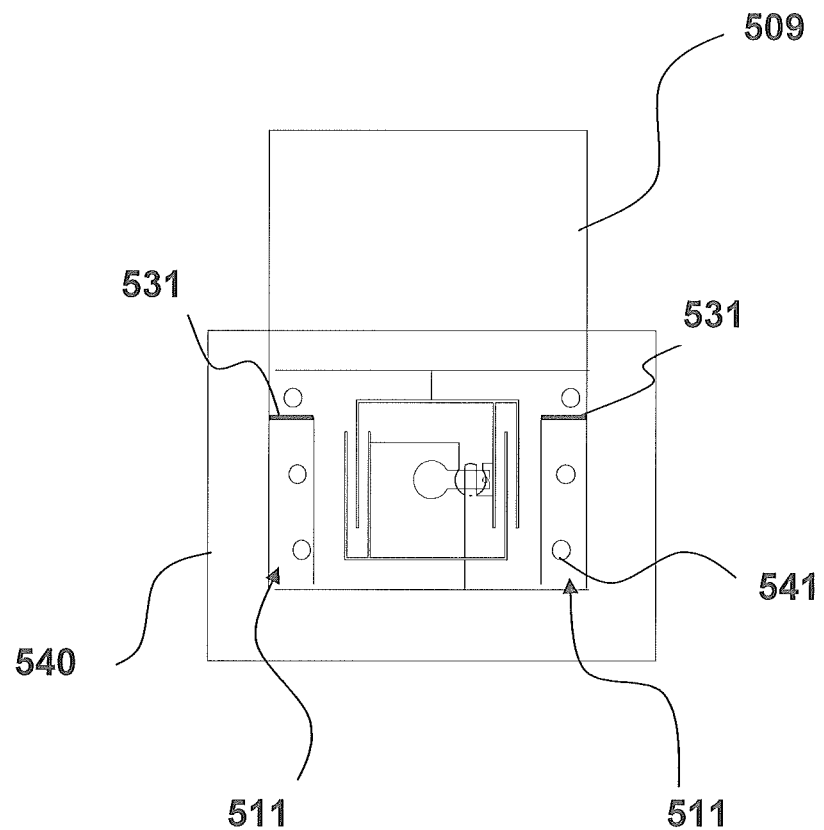
FIG. 27B is a plan view of a state in which the biosensor has been inserted into a sensor insertion component.

As shown in FIGS. 27A and 27B, the connector pins 541 consist of connector pins 541-A1, 541-B1, 541-C1, 541-A2, 541-B2, and 541-C2. These connector pins enter their continuity state via the connection terminals 511 of the inserted biosensor 504. By detecting this continuity state, the controller of the measurement device 100 (FIG. 1) can determine the installation state of the biosensor 504 with respect to the sensor insertion component 540. More specifically, the relation between the continuity state of the connector pins 541 and the installation state of the biosensor 504 with respect to the sensor insertion component 540 is as follows.

(1) When the biosensor 504 has only been inserted part of the way into the sensor insertion component 540 (such as the state shown in FIG. 27A)
   The connector pins 541-A1 and 541-B1 or the connector pins 541-A2 and 541-B2 are in their continuity state
(2) When the biosensor 504 has been inserted at an angle to the sensor insertion component 540
   The connector pins 541-A1 and 541-B1, and the connector pins 541-B2 and 541-C2, are in their continuity state, or
   The connector pins 541-A2 and 541-B2, and the connector pins 541-B1 and 541-C1, are in their continuity state
(3) When the biosensor 504 has been properly inserted into the sensor insertion component 540
   The connector pins 541-B1 and 541-C1, and the connector pins 541-B2 and 541-C2, are in their continuity state (the state shown in FIG. 27B)

The slits 531 are formed in the element substrate 509 so as to be positioned between the connector pins 541-A1 and 541-B1 that are the deepest in the insertion direction after 541-C1, and between 541-A2 and 541-B2 that are the deepest after 541-C2, when the biosensor 504 has been properly inserted into the sensor insertion component 540. The reason for providing these slits 531 is to improve the accuracy of detection of the installation state of the biosensor 504. For instance, even though the connector pins 541-A1 to C1 and 541-A2 to C2 are all in their continuity state, that does not necessarily mean that the biosensor 504 has been properly inserted all the way into the sensor insertion component 540, but as shown in FIG. 27B, if the slits 531 isolate the connector pin 541-A1 from 541-B1 and 541-C1, and isolate 541-A2 from 541-B2 and 541-C2, it can be correctly detected that the biosensor 504 has been properly inserted all the way into the sensor insertion component 540.

As discussed above, if it is determined from the continuity state of the connector pins 541 that the biosensor 504 has not been properly inserted into the sensor insertion component 540, the controller of the measurement device 100 (FIG. 1) detects an error, and a warning to the effect that the biosensor 504 has not been properly inserted may be displayed on the display component 2, or a specific warning sound may be issued, at a command from the controller. Also, as shown in FIG. 27B, if the biosensor 504 has been properly inserted into the sensor insertion component 540, this state is detected by the controller, and the fact that the biosensor 504 is properly inserted may be displayed on the display component 2, or a specific sound may be issued, by the controller.

5.2 Features of Biosensor

With the biosensor 504 pertaining to this embodiment, the connection terminals 511 are provided at an end in the width direction of the sensor, connector pins 541 that connect to the connection terminals 511 of the biosensor 504 respectively are provided to the sensor insertion component 540 provided to the sensor installation component 5 of the measurement device 100 (FIG. 1), and whether or not the biosensor 504 has been properly installed can be detected from the continuity state of these pins. With this configuration, accuracy can be improved in the positioning of the biosensor 504.

Also, the spacing of the pairs of connector pins 541 in the width direction increases closer to the front in the sensor insertion direction, and decreases toward the rear. This prevents the connector pins 541 from scratching the connection terminals 511 during sensor insertion.

Furthermore, providing the slits 531 at the upper part of the connection terminals 511 improves the accuracy of detection of the installation state of the biosensor 504.

Even if there are more connector pins 541 than in the above embodiment, the slits 531 may be formed so as to be located between two or more connector pins on the deeper side in the insertion direction and the other connector pins when the sensor insertion component 540 has been properly inserted into the sensor insertion component 540.

6. Embodiment 6

6.1 Cartridge Configuration

Figure 28A:
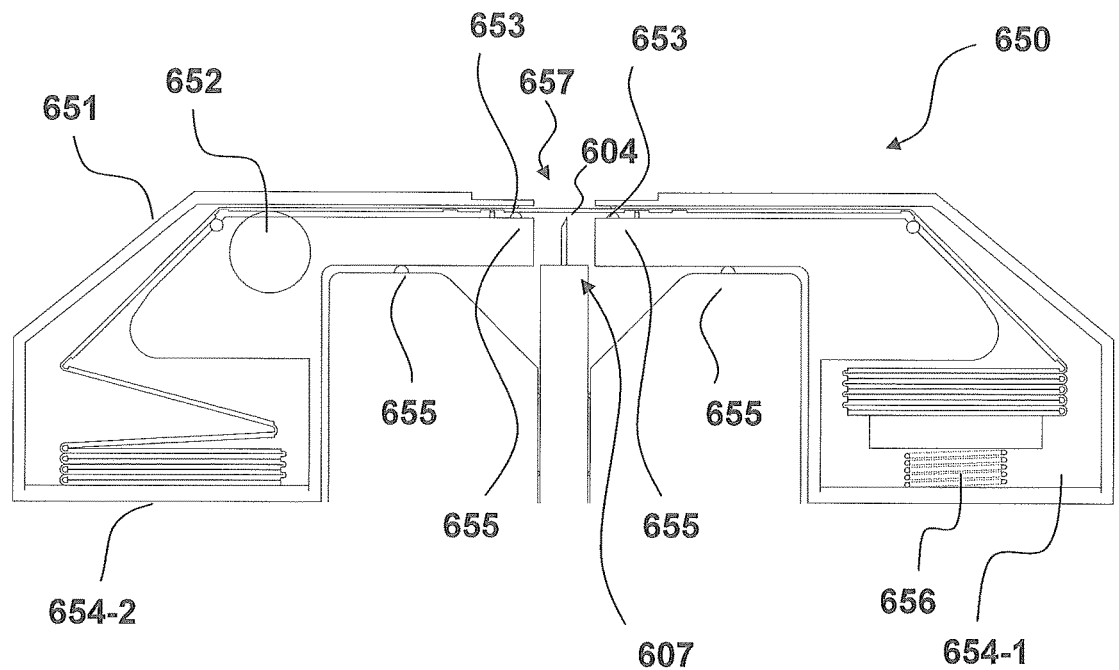
FIG. 28A is a cross section of a cartridge pertaining to Embodiment 6 of the present invention.
Figure 28B:
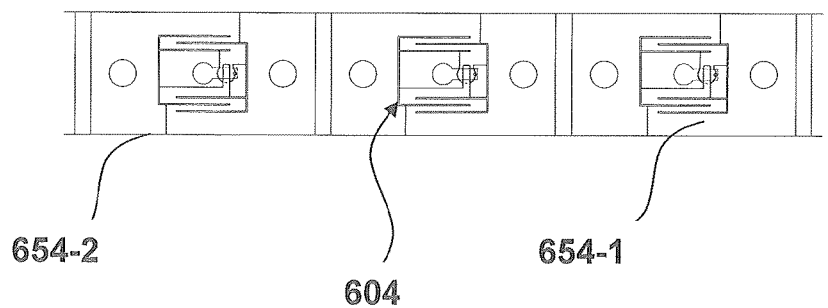
FIG. 28B is a top view of the cartridge.
Figure 29:
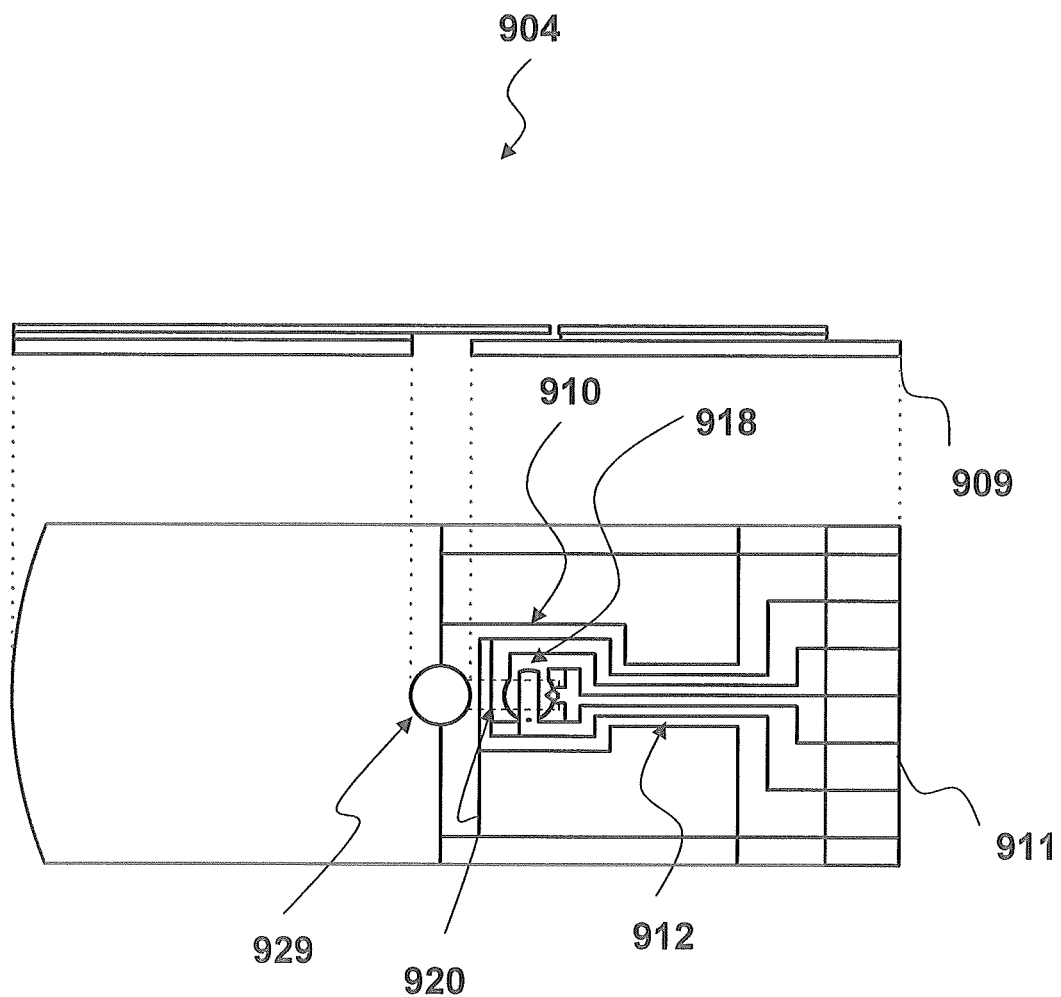
FIG. 29 is a diagram of the configuration of a conventional biosensor.
Figure 30:
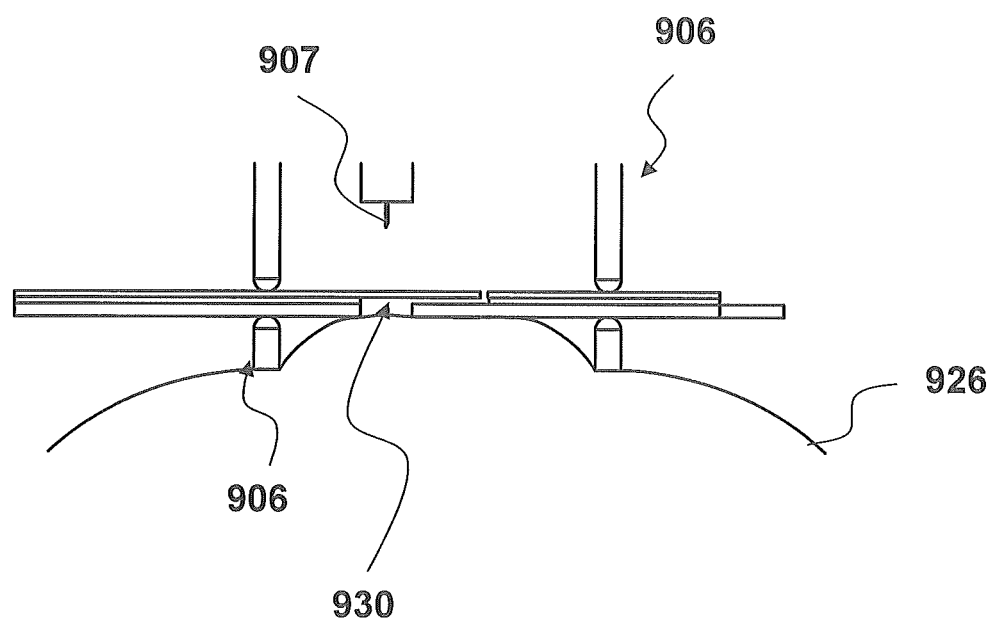
FIG. 30 is a cross section of the main components of a conventional biosensor and measurement device during the puncture operation.

FIG. 28A is a cross section of a cartridge 650 that is removably mounted in the measurement device 100 (FIG. 1) and holds biosensors such as those described in the above Embodiments 1 to 5, for example. FIG. 28B is a top view of the cartridge 650.

As shown in FIG. 28A, the cartridge 650 comprises a main case 651, a take-up roll 652 for moving sensors, connector pins 653, and an airtight sealant 655.

The main case 651 has an unused sensor holder 654-1 that holds unused sensors, and a used sensor holder 654-2 that holds used sensors.

The take-up roll 652 feeds out unused sensors 604 biased in the feed direction by a spring 656 from the unused sensor holder 654-1. The unused sensor 604 that has been fed out has its puncture component 657 punctured by a puncture needle 607, after which blood is deposited and measurement processing is carried out. The biosensor 604 that has undergone this measurement processing is sent as a used sensor to the used sensor holder 654-2. The take-up roll 652 is driven and rotated by a specific drive means at a command from a controller (not shown) of the measurement device 100 (FIG. 1).

The connector pins 653 is connected to a connection terminal (not shown) of the biosensor 604 to produce a continuity state, as described in the above embodiments.

The airtight sealant 655 is disposed so that a negative pressure component can be formed in the puncture component during the puncture operation, as described in the above embodiments.

6.2 Features of Cartridge

Providing the cartridge 650 as above makes the measurement device 100 more convenient to use, without the need to replace the biosensor 604 after a single puncture.

7. Other Embodiments

7.1

In the above embodiments, a biosensor and measurement device for measuring blood glucose level are described, but the biosensor and measurement device pertaining to the present invention are not limited to this, and can also be applied to the measurement of data related to lactic acid, cholesterol, uric acid, and other such biological information.

7.2

The configuration and processing details of the blood glucose level measurement device pertaining to Embodiments 1 to 6 above may be combined.

INDUSTRIAL APPLICABILITY

The biosensor and measurement device pertaining to the present invention can be utilized in the measurement of blood glucose levels, lactic acid levels, and so on, and are useful as medical devices and so forth.

REFERENCE SIGNS LIST 1 main case
2 display component
3 puncture button
4 biosensor
5 sensor installation component
6 negative pressure formation component
7 needle
8 needle movement component
9 element substrate
10 detector
11 connection terminal
12 continuity path
13 cutout
13-1 cutout
13-2 cutout
13-3 cutout
14 non-cutout part
15 lower plate
16 middle plate
17 upper plate
18 reaction component
19 puncture through-component
20 spacer
21 specimen supply route
22 puncture through-hole
23 narrow groove
24 cover
24-1 non-through-component
25 air hole
26 finger
27 upper cylinder
28 lower cylinder
29 puncture component
204 biosensor
209 element substrate
210 detector
211 connection terminal
211-1 working electrode
211-2 counter electrode
212 continuity path
213 cutout
304 biosensor
309 element substrate
310 detector
311 connection terminal
404 biosensor
409 element substrate
410 detector
411 connection terminal
411-1 working electrode
411-2 counter electrode
411-3 detecting electrode
411-4 Hct measurement electrode
440 sensor insertion component
441 connector pin
504 biosensor
509 element substrate
510 detector
511 connection terminal
531 slit
540 sensor insertion component
541 connector pin
604 biosensor
607 puncture needle
650 cartridge
652 take-up roll
653 connector pin
654-1 unused sensor holder
654-2 used sensor holder
655 airtight sealant
656 spring
657 puncture component

The invention claimed is:

1. A biosensor, comprising:
    an element substrate including a lower plate, a middle plate laminated over the lower plate, and an upper plate laminated over the middle plate;
    a detector configured to receive a specimen and detect a specific component contained in the specimen;
    a connection terminal provided over the element substrate and configured to acquire current corresponding to the specific component;
    a continuity path arranged to connect the connection terminal and the detector;
    a cutout formed on the lower plate, the middle plate and the upper plate respectively and along an outer periphery of the detector so as to surround two or more directions of the detector, and
    a non-cutout part formed on the lower plate, the middle plate, and the upper plate respectively,
    wherein the detector is formed within the cutout on the element substrate and bends upward, and
    a width of the non-cutout part formed on the middle plate and the upper plate respectively is narrower than a width of the non-cutout part formed on the lower plate.

2. The biosensor according to claim 1,
    wherein the detector has:
    a puncture component configured to acquire the specimen by insertion of a needle;
    a reaction component configured to generate current corresponding to the specific component in the specimen; and a specimen supply route linking the puncture component and the reaction component.

3. The biosensor according to claim 1, wherein the cutout is formed continuously so as to surround the detector except for a pull-out portion of the continuity path.

4. The biosensor according to claim 3, wherein the cutout is elliptical or circular in a plan view of the biosensor.

5. The biosensor according to claim 1, wherein the cutout is linear and is formed so as to surround four sides of the detector.

6. The biosensor according to claim 5, wherein the cutout is formed in a fork shape in a plan view of the biosensor in at least one of the long-side direction and the short-side direction of the biosensor.

7. The biosensor according to claim 2, wherein the puncture component is disposed in an approximate center of the detector.

8. The biosensor according to claim 2, wherein the puncture component is disposed offset by a specific distance from a center of the detector, and the specific distance is set on the basis of a distance from a center of a bulging part of a finger when the finger has been placed against the puncture component, to an end edge of the detector.

9. The biosensor according to claim 2, wherein the element substrate includes a lower plate and an upper plate laminated over the lower plate, the reaction component, the continuity path, and the connection terminal are provided on the lower plate, and the specimen supply route is provided between the lower plate and the upper plate.

10. The biosensor according to claim 9, wherein the cutout is formed continuously so as to surround the detector except for a pull-out portion for the continuity path, and the pull-out portion formed on the upper plate has a width that is narrower than the pull-out portion for the continuity path formed on the lower plate.

11. The biosensor according to claim 9, wherein the puncture component includes a through-component formed over the lower plate, and a non-through-component formed in a portion of the upper plate corresponding to the through-component.

12. The biosensor according to claim 2, wherein the element substrate includes a lower plate, a middle plate laminated over the lower plate, and an upper plate laminated over the middle plate, the reaction component, the continuity path, and the connection terminal are provided on the lower plate, and the specimen supply route is provided on the middle plate.

13. The biosensor according to claim 12, wherein the cutout is formed continuously so as to surround the detector except for a pull-out portion for the continuity path, and the pull-out portion formed on each of the upper plate and the middle plate has a width that is narrower than the pull-out portion for the continuity path formed on the lower plate.

14. The biosensor according to claim 12, wherein the puncture component includes a through-component formed on the lower plate and the middle plate respectively, and a non-through-component formed in the portion of the upper plate corresponding to the through-component.

15. The biosensor according to claim 1, wherein the connection terminal has a plurality of electrodes that are provided to both sides of the detector in a short-side direction of the biosensor, the plurality of electrodes including at least a working electrode and a counter electrode.

16. The biosensor according to claim 15, wherein the plurality of electrodes further includes a detecting electrode and an Hct electrode.

17. The biosensor according to claim 1, further comprising a non-cutout part to which the continuity path is provided.

18. The biosensor according to claim 1, further comprising wherein the element substrate includes a lower plate and an upper plate laminated over the lower plate, and the non-cutout part of the upper plate has narrower width than the non-cutout part of the lower plate.

* * * * *